US006803192B1

(12) United States Patent
Chen

(10) Patent No.: US 6,803,192 B1
(45) Date of Patent: Oct. 12, 2004

(54) B7-H1, A NOVEL IMMUNOREGULATORY MOLECULE

(75) Inventor: Lieping Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/451,291

(22) Filed: Nov. 30, 1999

(51) Int. Cl.$^7$ .............................. C12Q 1/68; C12P 1/00; C12P 21/04; C12N 15/00; C07H 21/04
(52) U.S. Cl. ..................... 435/6; 435/41; 435/71.1; 435/320.1; 435/325; 536/23.1
(58) Field of Search .................. 435/6, 71.1, 320.1, 435/41, 325; 536/23.1, 24.3

(56) References Cited

U.S. PATENT DOCUMENTS

| | | | | |
|---|---|---|---|---|
| 5,858,776 A | * | 1/1999 | Ostrand-Rosenberg | ...... 435/325 |
| 2002/0102651 A1 | * | 8/2002 | Freeman et al. | ........... 436/69.1 |

FOREIGN PATENT DOCUMENTS

| | | | | |
|---|---|---|---|---|
| WO | WO 01/07611 A2 | | 2/2001 | ........... C12N/15/12 |
| WO | WO 01/14556 | * | 3/2001 | ................. 536/23.1 |

OTHER PUBLICATIONS

Russell et al., J. Mol. Biol. 1994, vol. 244, pp 332–350.*
Juppner ; Bone; vol. 17, pp 39S–42S; 1995.*
Romanos et al; DNA Cloning 2: A Practical Approach, chapter 5, IRL Press, Oxford, 1995; pp 133–148.*
Azuma et al., "B70 antigen is a second ligand for CTLA-4 and CD28," Nature 366:76–79, 1993.
Bajorath et al., "Immunoglobulin fold characteristics of B7–1 (CD80) and B7–2 (CD86)," Protein Science 3:2148–2150, 1994.
Fargeas et al., "Identification of Residues in the v Domain of CD80 (B7–1) Implicated in Functional Interactions with CD28 ad CTLA4," J. Exp. Med. 182:667–675, 1995.
Freeman et al., "B7–1 and B7–2 Do Not Deliver Identical Costimulatory Signals, . . . Production of IL–4," Immunity 2:523–532, 1995.
Freeman et al., "B7, A New Member of the Ig Superfamily with Unique Expression on Activated and Neoplastic B Cells," The Journal of Immunology 143:2714–2722, 1989.
Freeman et al., Structure, Expression, and T Cell Costimulatory Activity of the Murine Homologue . . . Antigen B7, J. Exp. Med. 174:625–631, 1991.
Freeman et al., "Cloning of B7–2: A CTLA–4 Counter–Receptor that Costimulates Human T Cell Proliferation," Science 262:909–911, 1993.
Freeman et al., "Murine B7–2, an Alternative CTLA4 Counter–receptor that Costimulates T Cell Proliferation and Interleukin 2 Production," J. Exp. Med. 178:2185–2192, 1993.
Inaba et al., "The Tissue Distribution of the B7–2 Costimulator in Mice: Abundant Expression on Dendritic Cells . . . In Vitro," J. Exp. Med. 180:1849–1860, 1994.
NCBI Sequence Database Entry. Accession No. AA292201 (Aug. 8, 1997).
NCBI Sequence Database Entry. Accession No. AA823166 (Feb. 17, 1998).
NCBI Sequence Database Entry. Accession No. AA896104 (Apr. 6, 1998).

* cited by examiner

*Primary Examiner*—Jehanne Sitton
(74) *Attorney, Agent, or Firm*—Fish & Richardson P.C.

(57) ABSTRACT

The invention provides novel polypeptides useful for co-stimulating T cells, isolated nucleic acid molecules encoding them, vectors containing the nucleic acid molecules, and cells containing the vectors. Also included are methods of making and using these co-stimulatory polypeptides.

13 Claims, 17 Drawing Sheets

```
CCCACGCGTCCGCAGCTTCCCGAGGCTCCGCACCAGCCGCGCTTCTGTCCGCC
TGCAGGGCATTCCAGAAAGATGAGGATATTTGCTGTCTTTATATTCATGACCT
ACTGGCATTTGCTGAACGCATTTACTGTCACGGTTCCCAAGGACCTATATGTG
GTAGAGTATGGTAGCAATATGACAATTGAATGCAAATTCCCAGTAGAAAAAC
AATTAGACCTGGCTGCACTAATTGTCTATTGGGAAATGGAGGATAAGAACAT
TATTCAATTTGTGCATGGAGAGGAAGACCTGAAGGTTCAGCATAGTAGCTAC
AGACAGAGGGCCCGGCTGTTGAAGGACCAGCTCTCCCTGGGAAATGCTGCAC
TTCAGATCACAGATGTGAAATTGCAGGATGCAGGGGTGTACCGCTGCATGAT
CAGCTATGGTGGTGCCGACTACAAGCGAATTACTGTGAAAGTCAATGCCCCA
TACAACAAAATCAACCAAAGAATTTTGGTTGTGGATCCAGTCACCTCTGAAC
ATGAACTGACATGTCAGGCTGAGGGCTACCCAAGGCCGAAGTCATCTGGAC
AAGCAGTGACCATCAAGTCCTGAGTGGTAAGACCACCACCACCAATTCCAAG
AGAGAGGAGAAGCTTTTCAATGTGACCAGCACACTGAGAATCAACACAACA
ACTAATGAGATTTTCTACTGCACTTTTAGGAGATTAGATCCTGAGGAAAACCA
TACAGCTGAATTGGTCATCCCAGAACTACCTCTGGCACATCCTCCAAATGAA
AGGACTCACTTGGTAATTCTGGGAGCCATCTTATTATGCCTTGGTGTAGCACT
GACATTCATCTTCCGTTTAAGAAAAGGGAGAATGATGGATGTGAAAAAATGT
GGCATCCAAGATACAAACTCAAAGAAGCAAAGTGATACACATTTGGAGGAG
ACGTAATCCAGCATTGGAACTTCTGATCTTCAAGCAGGGATTCTCAACCTGTG
GTTTAGGGGTTCATCGGGGCTGAGCGTGACAAGAGGAAGGAATGGACCCGTG
GGATGCAGGCAATGTGGGACTTAAAAGGCCCAAGCACTGAAAATGGAACCT
GGCGAAAGCAGAGGAGGAGAATGAAGAAAGATGGAGTCAAACAGGGAGCC
TGGAGGGAGACCTTGATACTTTCAAATGCCTGAGGGGCTCATCGACGCCTGT
GACAGGGAGAAAGGATACTTCTGAACAAGGAGCCTCCAAGCAAATCATCCAT
TGCTCATCCTAGGAAGACGGGTTGAGAATCCCTAATTTGAGGGTCAGTTCCTG
CAGAAGTGCCCTTTGCCTCCACTCAATGCCTCAATTTCTTTTCTGCATGACTG
AGAGTCTCAGTGTTGGAACGGGACAGTATTTATGTATGAGTTTTTCCTATTTA
TTTTGAGTCTGTGAGGTCTTCTTGTCATGTGAGTGTGGTTGTGAATGATTTCTT
TTGAAGATATATTGTAGTAGATGTTACAATTTTGTCGCCAAACTAAACTTGCT
GCTTAATGATTTGCTCACATCTAGTAAAACATGGAGTATTTGTAAGGTGCTTG
GTCTCCTCTATAACTACAAGTATACATTGGAAGCATAAAGATCAAACCGTTG
GTTGCATAGGATGTCACCTTTATTTAACCCATTAATACTCTGGTTGACCTAAT
CTTATTCTCAGACCTCAAGTGTCTGTGCAGTATCTGTTCCATTTAAATATCAG
CTTTACAATTATGTGGTAGCCTACACACATAATCTCATTTCATCGCTGTAACC
ACCCTGTTGTGATAACCACTATTATTTTACCCATCGTACAGCTGAGGAAGCAA
ACAGATTAAGTAACTTGCCCAAACCAGTAAATAGCAGACCTCAGACTGCCAC
CCACTGTCCTTTTATAATACAATTTACAGCTATATTTTACTTTAAGCAATTCTT
TTATTCAAAAACCATTTATTAAGTGCCCTTGCAATATCAATCGCTGTGCCAGG
CATTGAATCTACAGATGTGAGCAAGACAAAGTACCTGTCCTCAAGGAGCTCA
TAGTATAATGAGGAGATTAACAAGAAAATGTATTATTACAATTTAGTCCAGT
GTCATAGCATAAGGATGATGCGAGGGGAAAACCCGAGCAGTGTTGCCAAGA
GGAGGAAATAGGCCAATGTGGTCTGGGACGGTTGGATATACTTAAACATCTT
AATAATCAGAGTAATTTTCATTTACAAAGAGAGGTCGGTACTTAAAATAACC
CTGAAAAATAACACTGGAATTCCTTTTCTAGCATTATATTTATTCCTGATTTGC
```

FIG. 1A

```
CTTTGCCATATAATCTAATGCTTGTTTATATAGTGTCTGGTATTGTTTAACAGT
TCTGTCTTTTCTATTTAAATGCCACTAAATTTTAAATTCATACCTTTCCATGAT
TCAAAATTCAAAAGATCCCATGGGAGATGGTTGGAAAATCTCCACTTCATCC
TCCAAGCCATTCAAGTTTCCTTTCCAGAAGCAACTGCTACTGCCTTTCATTCA
TATGTTCTTCTAAAGATAGTCTACATTTGGAAATGTATGTTAAAAGCACGTAT
TTTTAAAATTTTTTTCCTAAATAGTAACACATTGTATGTCTGCTGTGTACTTTG
CTATTTTTATTTATTTAGTGTTTCTTATATAGCAGATGGAATGAATTTGAAGT
TCCCAGGGCTGAGGATCCATGCCTTCTTTGTTTCTAAGTTATCTTTCCCATAGC
TTTTCATTATCTTTCATATGATCCAGTATATGTTAAATATGTCCTACATATACA
TTTAGACAACCACCATTTGTTAAGTATTTGCTCTAGGACAGAGTTTGGATTTG
TTTATGTTTGCTCAAAAGGAGACCCATGGGCTCTCCAGGGTGCACTGAGTCA
ATCTAGTCCTAAAAAGCAATCTTATTATTAACTCTGTATGACAGAATCATGTC
TGGAACTTTTGTTTTCTGCTTTCTGTCAAGTATAAACTTCACTTTGATGCTGTA
CTTGCAAAATCACATTTTCTTTCTGGAAATTCCGGCAGTGTACCTTGACTGCT
AGCTACCCTGTGCCAGAAAAGCCTCATTCGTTGTGCTTGAACCCTTGAATGCC
ACCAGCTGTCATCACTACACAGCCCTCCTAAGAGGCTTCCTGGAGGTTTCGA
GATTCAGATGCCCTGGGAGATCCCAGAGTTTCCTTTCCCTCTTGGCCATATTC
TGGTGTCAATGACAAGGAGTACCTTGGCTTTGCCACATGTCAAGGCTGAAGA
AACAGTGTCTCCAACAGAGCTCCTTGTGTTATCTGTTTGTACATGTGCATTTG
TACAGTAATTGGTGTGACAGTGTTCTTTGTGTGAATTACAGGCAAGAATTGTG
GCTGAGCAAGGCACATAGTCTACTCAGTCTATTCCTAAGTCCTAACTCCTCCT
TGTGGTGTTGGATTTGTAAGGCACTTTATCCCTTTTGTCTCATGTTTCATCGTA
AATGGCATAGGCAGAGATGATACCTAATTCTGCATTTGATTGTCACTTTTTGT
ACCTGCATTAATTTAATAAAATATTCTTATTTATTTTGTTACTTGGTAAAAAA
AAAAAAAAAAAAAAAAAAAAAAAAAAAAAAAAA
```

FIG. 1B

Signal peptide
1   MRIFAVFIEMTYWHLLNAFTVTVPKDLYVVEYGSNMTIECKFPVEKQLDL
                                            *
                              Ig-V-like
51  AALIVYWEMEDKNIIQFVHGEEDLKVQHSSYRQRARLLKDQLSLGNAALQ 101 ITDVKLQDAGVYRCMISYGGADYKRITVKVNAPYNKINQRILVVDPVTSE
                              Ig-C-like
151 HELTCQAEGYPKAEVIWTSSDHQVLSGKTTTTNSKREEKLFNVTSTLRIN
                                      *                    *
201 TTTNEIFYCTFRRLDPEENHTAELVIPELPLAHPPNERTHLVILGAILLC
                      *                              TM
251 LGVALTFIFRLRKGRMMDVKKCGIQDTNSKKQSDTHLEET

FIG. 2A

```
                              *
B7-H1  50  VEYGSNMTIECKFPVEKQLDLAALIVYWEM
B7-1   43     KEVATLSCGHNVS-VEELAQTRIYWQK
B7-2   30  AYFNETADLPCQFANSQNQSLSELVVFWQD

80  EDKNIIQFVHGEED-LKVQHSSYRQRARLL
       68  EKKMVLTMMSGDMN----IWPEYKNRTIFD
       60  QENLVLNEVYLGKEKFDSVHSKYMGRTSFD

*
       89  KDQLSLGNAALQITDVKLQDAGVYRCMISY
       95  IT----NNLSIVILALRPSDEGTYECVVLK
       90  S-----DSWTLRLHNLQIKDKGLYQCIIHH

119  GGADYKR----ITVKVNAPYNKINQRILVV
      121  YEKDAFKREHLAEVTLSVKADFPTPSISDF
      115  KKPTGMIRIHQMNSELSVLANFSQPEIVPI

*
      145  DPVTSEHEL--TC-QAEGYPKA-EVIWTSS
      151  EIPTSNIRR-IICSTSGGFPEP-HLSWLEN
      145  SNITENVYINLTCSSIHGYPEPKKMSVLLR

171  DHQ---VLSGKTTTTNSKREEKLFNVTSTL
      179  GE----ELNAINTTVSQDPETELYAVSSKL
      175  TKNSTIEYDGIMQK-SQDNVTELYDVSISL

*
      198  RIN---TTTNEIFYCTFRRLDPEENHTAEL
      205  DFN---MTTNHSFMCLIKYGHLRVN--QTF
      204  SVSFPDVTSNMTIFCILETDKTRLLS-SPE

226  VIPELPLAHPPNERT
      230  NWNTTKQEHFPDNLL
      233  SHELEDPQPPPDHIP                FIG. 2B
```

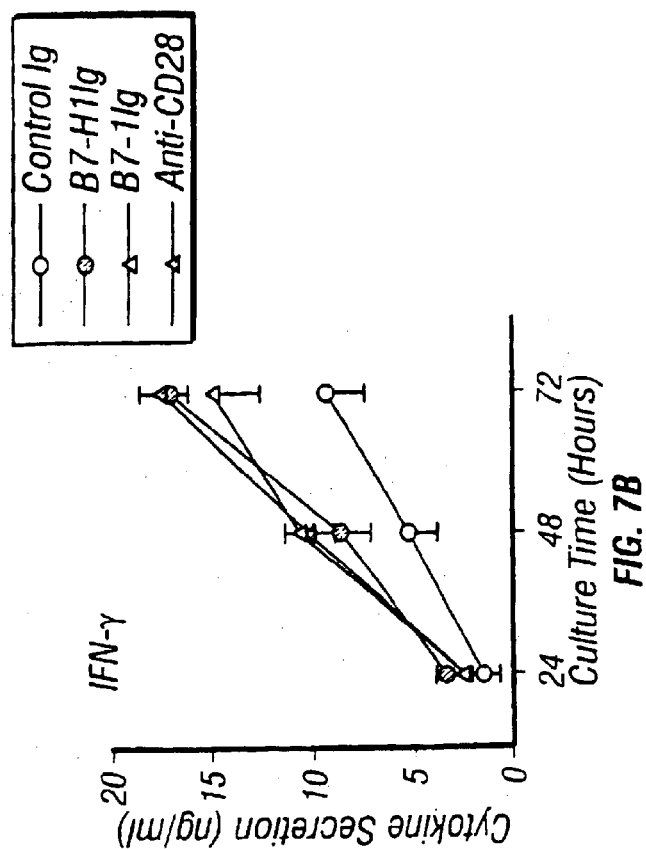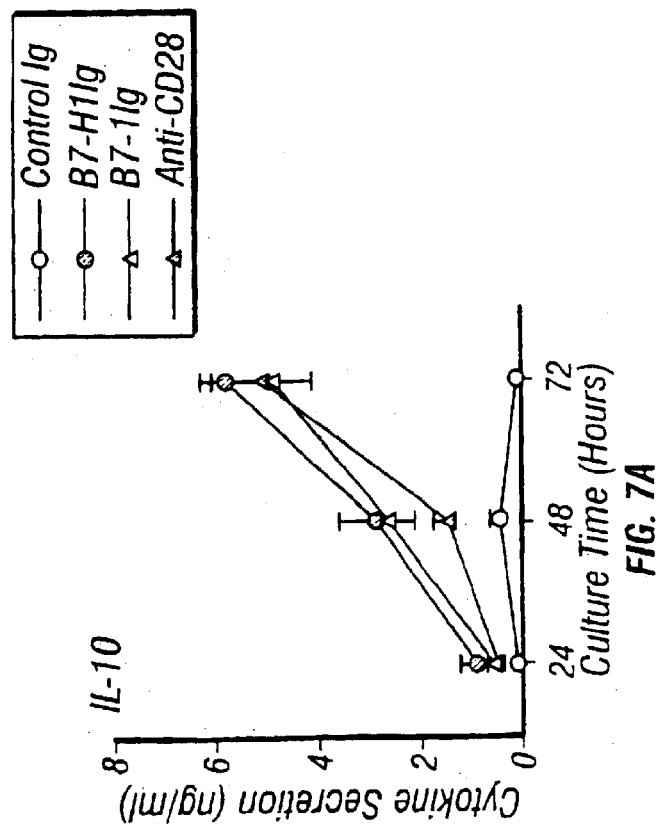

```
ATGAGGATATTTGCTGGCATTATATTCACAGCCTGCTGTCACTTGCTACGGGC
GTTTACTATCACGGCTCCAAAGGACTTGTACGTGGTGGAGTATGGCAGCAAC
GTCACGATGGAGTGCAGATTCCCTGTAGAACGGGAGCTGGACCTGCTTGCGT
TAGTGGTGTACTGGGAAAAGGAAGATGAGCAAGTGATTCAGTTTGTGGCAGG
AGAGGAGGACCTTAAGCCTCAGCACAGCAACTTCAGGGGGAGAGCCTCGCT
GCCAAAGGACCAGCTTTTGAAGGGAAATGCTGCCCTTCAGATCACAGACGTC
AAGCTGCAGGACGCAGGCGTTTACTGCTGCATAATCAGCTACGGTGGTGCGG
ACTACAAGCGAATCACGCTGAAAGTCAATGCCCCATACCGCAAAATCAACCA
GAGAATTTCCGTGGATCCAGCCACTTCTGAGCATGAACTAATATGTCAGGCC
GAGGGTTATCCAGAAGCTGAGGTAATCTGGACAAACAGTGACCACCAACCCG
TGAGTGGGAAGAGAAGTGTCACCACTTCCCGGACAGAGGGGATGCTTCTCAA
TGTGACCAGCAGTCTGAGGGTCAACGCCACAGCGAATGATGTTTTCTACTGT
ACGTTTTGGAGATCACAGCCAGGGCAAAACCACACAGCGGAGCTGATCATCC
CAGAACTGCCTGCAACACATCCTCCACAGAACAGGACTCACTGGGTGCTTCT
GGGATCCATCCTGTTGTTCCTCATTGTAGTGTCCACGGTCCTCCTCTTCTTGAG
AAAACAAGTGAGAATGCTAGATGTGGAGAAATGTGGCGTTGAAGATACAAG
CTCAAAAAACCGAAATGATACACAATTCGAGGAGACGTAA
```

FIG. 10

```
MRIFAGIIFTACCHLLRAFTITAPKDLYVVEYGSNVTMECRFPVERELDLLALVV
YWEKEDEQVIQFVAGEEDLKPQHSNFRGRASLPKDQLLKGNAALQITDVKLQDA
GVYCCIISYGGADYKRITLKVNAPYRKINQRISVDPATSEHELICQAEGYPEAEVI
WTNSDHQPVSGKRSVTTSRTEGMLLNVTSSLRVNATANDVFYCTFWRSQPGQN
HTAELIIPELPATHPPQNRTHWVLLGSILLFLIVVSTVLLFLRKQVRMLDVEKCGV
EDTSSKNRNDTQFEET
```

FIG. 11 anti-mB7-1-FITC ⟶ anti-mB7H/PE ⟶

B7-H1, A NOVEL IMMUNOREGULATORY MOLECULE

STATEMENT AS TO FEDERALLY SPONSORED RESEARCH

Work on this invention was supported by NTH Grant Number CA79915. Therefore the government may have certain rights in the invention.

BACKGROUND OF THE INVENTION

The invention is generally in the field of immunoregulation, and specifically T cell response regulation.

Mammalian T lympphocytes recognize antigenic peptides bound to major histocompatibility complex (MHC) molecules on the surface of antigen presenting cells (APC). The antigenic peptides are generated by proteolytic degradation of protein antigens within the APC. The interaction of the T cells with the APC and the susbsequent response of the T cells are qualitatively and quantitatively regulated by interactions between cell surface receptors on the T cells with both soluble mediators and ligands on the surface of APC.

SUMMARY OF THE INVENTION

The invention is based on the cloning of human and mouse cDNA molecules encoding novel homologous molecules that co-stimulate the T cell responses of both species and the functional characterization of the polypeptides that the cDNA molecules encode. The human polypeptide is designated hB7-H1 and the mouse polypeptide mB7-H1. Text that refers to B7-H1 without specifying human versus mouse is pertinent to both forms of B7-H1. The invention features DNA molecules encoding the hB7-H1, mB7-H1 polypeptides, functional fragments of the polypeptides, and fusion proteins containing the polypeptides or functional fragments of them, hB7-H1 and mB7-H1 and functional fragments of both, vectors containing the DNA molecules, and cells containing the vectors. Also included in the invention are antibodies that bind to the B7-H1 polypeptides. The invention features in vitro, in vivo, and ex vivo methods of co-stimulating T cell responses, methods of screening for compounds that inhibit or enhance T cell responses, and methods for producing the above polypeptides and fusion proteins.

Specifically the invention features an isolated DNA including: (a) a nucleic acid sequence that (i) encodes a B7-H1 polypeptide with the ability to co-stimulate a T cell, and (ii) hybridizes under stringent conditions to the complement of a sequence that encodes a polypeptide with an amino acid sequence with SEQ ID NO:1 or SEQ ID NO:3; or (b) a complement of this nucleic acid sequence. The nucleic acid sequence included in the isolated DNA will be at least 10 bp, 15 bp, 25 bp, 50 bp, 75 bp, 100 bp, 125 bp, 150 bp, 175 bp, 200 bp, 250 bp, 300 bp, 350 bp, 400 bp, 450 bp, 500 bp, 550 bp, 600 bp, 650 bp, 750, bp 800 bp, 850 bp, or 870 bp long. The nucleic acid sequence can encode a B7-H1 polypeptide that includes an amino sequence with SEQ ID NO:1 or SEQ ID NO:3 or it can have a nucleotide sequences with SEQ ID NO:2 or SEQ ID NO:4. The nucleic acid sequence can also encode functional fragments of these B7-H1 polypeptides.

The invention also embodies an isolated B7-H1 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3. The B7-H1 polypeptide can include an amino sequence of amino acid residue 23 to amino acid residue 290 of SEQ ID NO:1 or SEQ ID NO:3. The invention also encompasses B7-H1 polypeptides that include an amino acid sequence with SEQ ID NO:1 or SEQ ID NO:3, or either of these amino acid sequences but differing solely by one or more conservative substitutions. The polypeptides of the invention include fusion proteins containing a first domain and at least one additional domain. The first domain can be any of the B7-H1 polypeptides described above or a functional fragment of any of these polypeptides. The at least one additional domain can be a heterologous targeting or leader sequence, an amino acid sequence that facilitates purification, detection, or solubility of the fusion protein. The second domain can be, for example, all or part of an immunoglobulin (Ig) heavy chain constant region. Also included are isolated nucleic acid molecules encoding the fusion proteins.

The invention features vectors containing any of the DNAs of the invention and nucleic acid molecules encoding the fusion proteins of the invention. The vectors can be expression vectors in which the nucleic acid coding sequence or molecule is operably linked to a regulatory element which allows expression of the nucleic acid sequence or molecule in a cell. Also included in the invention are cells (e.g., mammalian, insect, yeast, fungal, or bacterial cells) containing any of the vectors of the invention.

Another embodiment of the invention is a method of co-stimulating a T cell that involves contacting the T cell with any of the B7-H1 polypeptides of the invention, functional fragments thereof or fusion proteins of the invention; these 3 classes of molecule are, for convenience, designated "B7-H1 agents". The contacting can be by culturing any of these B7-H1 agents with the T cell in vitro. Alternatively, the T cell can be in a mammal and the contacting can be, for example, by administering any of the B7-H1 agents to the mammal or administering a nucleic acid encoding the B7-H1 agent to the mammal. In addition, the method can be an ex vivo procedure that involves providing a recombinant cell which is the progeny of a cell obtained from the mammal and has been transfected or transformed ex vivo with a nucleic acid encoding any of the B7-H1 agents so that the cell expresses the B7-H1 agent; and administering the cell to the mammal. In this ex vivo procedure, the cell can be an antigen presenting cell (APC) that expresses the B7-H1 agent on its surface. Furthermore, prior to administering to the mammal, the APC can be pulsed with an antigen or an antigenic peptide. In any of the above methods, the mammal can be suspected of having, for example, an immunodeficiency disease, an inflammatory condition, or an autoimmune disease.

The invention includes a method of identifying a compound that inhibits an immune response. The method involves: providing a test compound; culturing, together, the compound, one or more B7-H1 agents, a T cell, and a T cell activating stimulus; and determining whether the test compound inhibits the response of the T cell to the stimulus, as an indication that the test compound inhibits an immune response. The invention also embodies a method of identifying a compound that enhances an immune response. The method involves: providing a test compound; culturing, together, the compound, one or more B7-H1 agents, a T cell, and a T cell activating stimulus; and determining whether the test compound enhances the response of the T cell to the stimulus, as an indication that the test compound enhances an immune response. In both these methods, the stimulus can be, for example, an antibody that binds to a T cell receptor or a CD3 polypeptide. Alternatively, the stimulus can be an alloantigen or an antigenic peptide bound to a major histocompatibility complex (MHC) molecule on the surface of an antigen presenting cell (APC). The APC can be transfected or transformed with a nucleic acid encoding the B7-H1agent and the B7-H1 agent can be expressed on the surface of the APC.

The invention also features an antibody (e.g., a polyclonal or a monoclonal antibody) that binds to any of the B7-H1 polypeptides of the invention, e.g., the polypeptide with SEQ ID NO:1 or SEQ ID NO:3.

The invention also features a method of producing any of the B7-H1 polypeptides of the invention, functional fragments thereof, or fusion proteins of the invention. The method involves culturing a cell of the invention and purifying the relevant B7-H1 protein from the culture.

"Polypeptide" and "protein" are used interchangeably and mean any peptide-linked chain of amino acids, regardless of length or post-translational modification. The invention also features B7-H1 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The term "isolated" polypeptide or peptide fragment as used herein refers to a polypeptide or a peptide fragment which either has no naturally-occurring counterpart (e.g., a peptidomimetic), or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide or nucleic acid is "isolated."

An isolated polypeptide (or peptide fragment) of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

An "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as: a cDNA where the corresponding genomic DNA has introns and therefore a different sequence; a genomic fragment; a fragment produced by polymerase chain reaction (PCR); a restriction fragment; a DNA encoding a non-naturally occurring protein, fusion protein, or fragment of a given protein; or a nucleic acid which is a degenerate variant of a naturally occurring nucleic acid. In addition, it includes a recombinant nucleotide sequence that is part of a hybrid gene, i.e., a gene encoding a fusion protein. Also included is a recombinant DNA that includes a portion of SEQ ID NO:2, SEQ ID NO:4, or SEQ ID NO:5.

As used herein, a polypeptide that "co-stimulates" a T cell is a polypeptide that, upon interaction with a cell-surface molecule on the T cell, enhances the response of the T cell. The T cell response that results from the interaction will be greater than the response in the absence of the polypeptide. The response of the T cell in the absence of the co-stimulatory polypeptide can be no response or it can be a response significantly lower than in the presence of the co-stimulatory polypeptide. It is understood that the response of the T cell can an effector, helper, or suppressive response.

As used herein, an "activating stimulus" is a molecule that delivers an activating signal to a T cell, preferably through the antigen specific T cell receptor (TCR). The activating stimulus can be sufficient to elicit a detectable response in the T cell. Alternatively, the T cell may require co-stimulation (e.g., by a B7-H1 polypeptide) in order to respond detectably to the activating stimulus. Examples of activating stimuli include, without limitation, antibodies that bind to the TCR or to a polypeptide of the CD3 complex that is physically associated with the TCR on the T cell surface, alloantigens, or an antigenic peptide bound to a MHC molecule.

As used herein, a "fragment" of a B7-H1 polypeptide is a fragment of the polypeptide that is shorter than the full-length polypeptide. Generally, fragments will be five or more amino acids in length. An antigenic fragment has the ability to be recognized and bound by an antibody.

As used herein, a "functional fragment" of a B7-H1 polypeptide is a fragment of the polypeptide that is shorter than the full-length polypeptide and has the ability to co-stimulate a T cell. Methods of establishing whether a fragment of an B7-H1 molecule is functional are known in the art. For example, fragments of interest can be made by either recombinant, synthetic, or proteolytic digestive methods. Such fragments can then be isolated and tested for their ability to co-stimulate T cells by procedures described herein.

As used herein, "operably linked" means incorporated into a genetic construct so that expression control sequences effectively control expression of a coding sequence of interest.

As used herein, the term "antibody" refers not only to whole antibody molecules, but also to antigen-binding fragments, e.g., Fab, F(ab')$_2$, Fv, and single chain Fv fragments. Also included are chimeric antibodies.

As used herein, an antibody that "binds specifically" to an isolated B7-H1 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3, is an antibody that does not bind to B7-1 or B7-2 polypeptides.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing immune responses in mammalian subjects, will be apparent from the following description, from the drawings and from the claims.

BRIEF DESCRIPTION OF THE DRAWINGS

FIG. 1 is a depiction of the nucleotide sequence of a cDNA fragment (SEQ ID NO: 5) that includes the coding sequence (nucleotides 73-942 of SEQ ID NO:5) (SEQ ID NO:2) of hB7-H1.

FIG. 2a is a depiction of the amino acid sequence of hB7-H1 (SEQ ID NO:1).

FIG. 2b is a depiction of the amino acid sequences of the extracellular domains of hB7-H1, (SEQ ID NO:10) B7-1, (SEQ ID NO:11) and B7-2 (SEQ ID NO:12) aligned for maximum homology. Identical amino acid residues are shaded in bold and conserved residues are boxed.

FIG. 7d is a line graph showing the ability of various concentrations of hB7-H1 to co-stimulate the production by human T cells responding to immobilized antibody specific for CD3 of IL-10.

FIG. 10 is a depiction of the nucleotide sequence of cDNA encoding mB7-H1 (SEQ ID NO:4).

FIG. 11 is a depiction of the amino acid sequence of mB7-H1 (SEQ ID NO:3).

DETAILED DESCRIPTION

Figure 3:
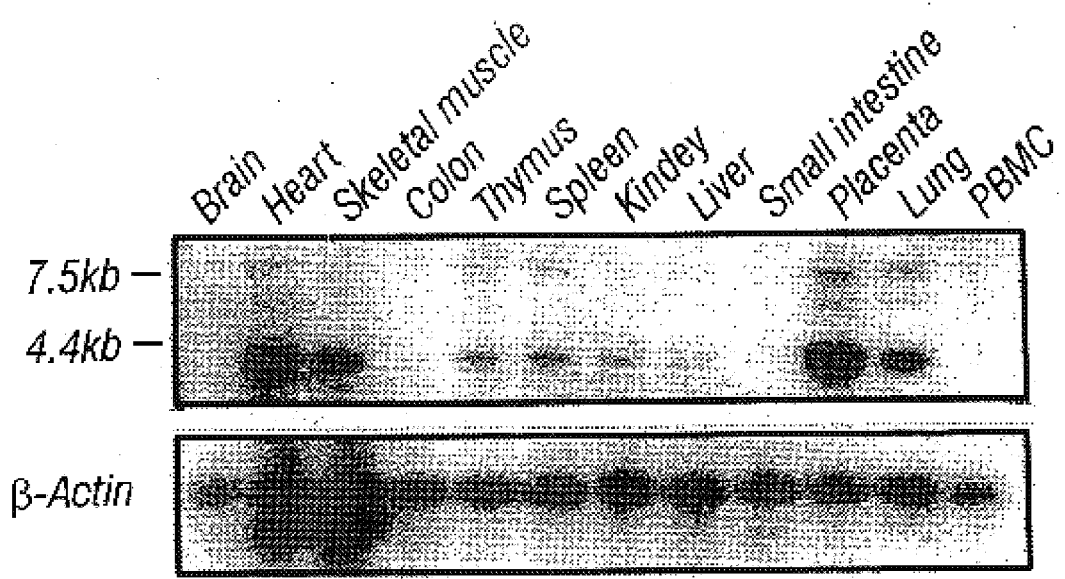
FIG. 3 is a photograph of a Northern blot showing expression of hB7-H1 mRNA in various human tissues.

Using PCR primers with sequences derived from an expressed sequence tag (EST) that had significant homology to human B7-1 and B7-2 and a human cDNA library as a source of template, cDNA sequences corresponding to regions of a transcript 5' and 3' of the EST were identified. A cDNA molecule (SEQ ID NO:5) that included a open reading frame (orf) (SEQ ID NO:2) encoding a novel B7-related molecule was then generated using PCR primers with sequences derived from the 3' and 5' ends and cloned.

Translation of the cDNA sequence indicated that the polypeptide (SEQ ID NO:1) that it encoded (hB7-H1) is a type I transmembrane protein of 290 amino acids containing an immunoglobulin (Ig) V-like domain, Ig C-like domain, a transmembrane domain and a cytoplasmic domain of 30 amino acids. Northern blot analysis showed strong expression of the gene encoding hB7-H1 in heart, skeletal muscle, placenta, and lung, and weak expression in thymus, spleen, kidney, and liver. Expression was undetectable in brain, colon, small intestine, and peripheral blood mononuclear cells (PBMC).

Using an antiserum produced by immunization of mice with a recombinantly produced fusion protein that included the hB7-H1 protein, expression by fluorescence flow cytometry indicated negligible expression on resting T and B cells. On the other hand, about 16% of CD14+monocytes constitutively expressed the molecule on their surface. Activation of T cells increased expression such that about 30% expressed cell-surface hB7-H1. Activation resulted in about 90% of monocytes expressing hB7-1H, but only about 6% of B cells expressed it after activation.

Transfection of 293 cells resulted in an hB7-H1 expressing cell line (hB7-H1/293) which was used for binding experiments. These experiments and others with a CD28 expressing cell line indicated that neither CTLA4, ICOS, nor CD28 were receptors for hB7-H1.

In vitro experiments with isolated human T cells and the hB7-H1-containing fusion protein indicated that hB7-H1 had no direct activity on T cells, it enhanced ("co-stimulated") T cell proliferative responses induced by both antibody specific for human CD3 and MHC alloantigens. This co-stimulatory activity was significantly more potent when the hB7-H1 was immobilized in the plastic tissue culture wells used for the cultures than when it as in solution. Similar experiments indicated that hB7-H1 had a dramatic and selective enhancing effect on the production of interleukin (IL)-10 induced by T cell activation. Moreover this IL-10 enhancing activity appeared to be dependent on at least low amounts of IL-2. Analysis of T cells activated by anti-CD3 antibody and hB7-H1Ig indicated that hB7-H1 enhances apoptosis and expression of Fas and FasL In addition, using a strategy essentially the same as that used to clone hB7-H1 cDNA, a cDNA molecule containing an orf encoding mouse B7-H1 (mB7-H1) was cloned, the nucleotide sequence of the orf (SEQ ID NO:4) was obtained, and the amino acid sequence of the encoded sequence (SEQ ID NO:3) was derived. mB7-H1 is exactly the same length (290 amino acids) as hB7-H1 and has the same domain structure.

B7-H1 can be useful as an augmenter of immune responses both in vivo and in vitro. Furthermore, in light of (a) its ability to selectively enhance IL-10 production, (b) its ability to enhance apoptosis, and (c) is expression in placenta and lung, both organs normally protected from unneeded cellular-mediated immune and inflammatory responses, B7-H1 can be useful in controlling pathologic cell-mediated conditions (e.g., those induced by infectious agents such *Mycobacterium tuberculosis* or *M leprae*) or other pathologic cell-mediated responses such as those involved in autoimmune diseases (e.g., rheumatoid arthritis (RA), multiple sclerosis (MS), or insulin-dependent diabetes mellitus (IDDM)).

B7-H1 Nucleic Acid Molecules

The B7-H1 nucleic acid molecules of the invention can be cDNA. genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions the membrane forms would not be soluble.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:1 and 3). In addition, these nucleic acid molecules are not limited to coding sequences, e.g., they can include some or all of the non-coding sequences that lie upstream or downstream from a coding sequence. They include, for example, the nucleic acid molecule with SEQ ID NO:5.

The nucleic acid molecules of the invention can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

In addition, the isolated nucleic acid molecules of the invention encompass segments that arc not found as such in the natural state. Thus, the invention encompasses recombinant nucleic acid molecules, (for example, isolated nucleic acid molecules encoding hB7-H1 or mB7-H1) incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

Certain nucleic acid molecules of the invention are antisense molecules or are transcribed into antisense molecules. These can be used, for example, to down-regulate translation of B7-H1 mRNA within a cell.

Techniques associated with detection or regulation of genes are well known to skilled artisans and such techniques can be used to diagnose and/or treat disorders associated with aberrant B7-H1 expression. Nucleic acid molecules of the invention are discussed further below in the context of their therapeutic utility.

A B7-H1 family gene or protein can be identified based on its similarity to the relevant B7-H 1 gene or protein, respectively. For example, the identification can be based on sequence identity. The invention features isolated nucleic acid molecules which are at least 50% (or 55%, 65%, 75%, 85%, 95%, or 98%) identical to: (a) a nucleic acid molecule that encodes the polypeptide of SEQ ID NO:1 or 3; (b) the nucleotide sequence of SEQ ID NO:2 or 4; or (c) a nucleic acid molecule which includes a segment of at least 30 (e.g., at least 50, 60, 100, 125, 150, 175, 200, 250, 300, 325, 350, 375, 400, 425, 450, 500, 550, 600, 650, 700, 800, or 865) nucleotides of SEQ ID NO:2 or SEQ ID NO:4.

The determination of percent identity between two sequences is accomplished using the mathematical algorithm of Karlin and Altschul, *Proc. Natl. Acad. Sci. USA* 90, 5873–5877, 1993. Such an algorithm is incorporated into the BLASTN and BLASTP programs of Altschul et al. (1990) *J Mol. Biol.* 215,403–410. BLAST nucleotide searches are performed with the BLASTN program, score=100, wordlength=12 to obtain nucleotide sequences homologous to B7-H1-encoding nucleic acids. BLAST protein searches are performed with the BLASTP program, score=50, wordlength=3 to obtain amino acid sequences homologous to B7-H1. To obtain gapped alignments for comparative purposes, Gapped BLAST is utilized as described in Altschul et al. (1997) *Nucleic Acids Res.* 25, 3389–3402. When utilizing BLAST and Gapped BLAST programs, the default parameters of the respective programs (e.g., XBLAST and NBLAST) are used (See http://www.ncbi.nlm.nih.gov).

Hybridization can also be used as a measure of homology between two nucleic acid sequences. A B7-H1-encoding nucleic acid sequence, or a portion thereof, can be used as hybridization probe according to standard hybridization techniques. The hybridization of a B7-H1 probe to DNA from a test source (e.g., a mammalian cell) is an indication of the presence of B7-H1 DNA in the test source. Hybridization conditions are known to those skilled in the art and can be found in Current Protocols in Molecular Biology, John Wiley & Sons, N.Y., 6.3.1–6.3.6, 1991. Moderate hybridization conditions are defined as equivalent to hybridization in 2× sodium chloride/sodium citrate (SSC) at 30° C., followed by one or more washes in 1 × SSC, 0.1% SDS at 50–60° C. Highly stringent conditions are defined as equivalent to hybridization in 6× sodium chloride/sodium citrate (SSC) at 45° C., followed by one or more washes in 0.2× SSC, 0.1% SDS at 50–65° C.

The invention also encompasses: (a) vectors that contain any of the foregoing B7-H1-related coding sequences and/or their complements (that is, "antisense" sequence); (b) expression vectors that contain any of the foregoing B7-H1-related coding sequences operatively associated with any transcriptional/translational regulatory elements (examples of which are given below) necessary to direct expression of the coding sequences; (c) expression vectors containing, in addition to sequences encoding a B7-H1 polypeptide, nucleic acid sequences that are unrelated to nucleic acid sequences encoding B7-H1, such as molecules encoding a reporter, marker, or a signal peptide, e.g., fused to B7-H1; and (d) genetically engineered host cells that contain any of the foregoing expression vectors and thereby express the nucleic acid molecules of the invention.

Recombinant nucleic acid molecules can contain a sequence encoding hB7-H1 or mB7-H1, or B7-H1 having an heterologous signal sequence. The full length B7-H1 polypeptide, a domain of B7-H1, or a fragment thereof may be fused to additional polypeptides, as described below. Similarly, the nucleic acid molecules of the invention can encode the mature form of B7-H1 or a form that includes an exogenous polypeptide which facilitates secretion.

The transcriptional/translational regulatory elements referred to above and which are further described below, include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH). thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a B7-H1 polypeptide and the second portion being, for example, the reporter described above or an Ig constant region or part of an Ig constant region, e.g., the CH2 and CH3 domains of IgG2a.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding B7-H1 (contained within SEQ ID NOS:1 or 3); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing B7-H1 nucleotide sequences; or mammalian cell systems (for example, COS, CHO, BHK, 293, VERO, HeLa, MDCK, W138, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector.

Polyneitides and Polypeptide Fragments

The polypeptides of the invention include hB7-H1, mB7-H1, and functional fragments of these polypeptides. The polypeptides embraced by the invention also include fusion proteins which contain either full-length B7-H1 or a functional fragment of it fused to unrelated amino acid sequence. The unrelated sequences can be additional functional domains or signal peptides. Signal peptides are described in greater detail and exemplified below.

The polypeptides can be purified from natural sources (e.g., blood, serum plasma, tissues or cells such as T cells or any cell that naturally produces B7-H1). Smaller peptides (less than 50 amino acids long) can also be conveniently synthesized by standard chemical means. In addition, both polypeptides and peptides can be produced by standard in vitro recombinant DNA techniques and in vivo recombination/genetic recombination (e.g., transgenesis), using the nucleotide sequences encoding the appropriate polypeptides or peptides. Methods well known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Polypeptides and fragments of the invention also include those described above, but modified for in vivo use by the addition, the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can he covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to co-stimulate T cells in a manner qualitatively identical to that of the B7-H1 functional peptide fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Therapy

The methods of the invention involve contacting a T cell with a B7-H1 molecule of the invention, or a functional fragment thereof, in order to co-stimulate the T cell. The contacting can occur before, during, or after activation of the T cell. Contacting of the T cell with the B7-H1 polypeptide will preferably be at substantially the same time as activation. Activation can be, for example, by exposing the T cell to an antibody that binds to the TCR or one of the polypeptides of the CD3 complex that is physically associated with the TCR. Alternatively, the T cell can be exposed to either an alloantigen (e.g., a MHC alloantigen) on, for example, an antigen presenting cell (APC) (e.g., a dendritic cell, a macrophage, a monocyte, or a B cell) or an antigenic peptide produced by processing of a protein antigen by any of the above APC and presented to the T cell by MHC molecules on the surface of the APC. The T cell can be a CD4+T cell or a CD8+T cell. The B7-H1 molecule can be added to the solution containing the cells, or it can be expressed on the surface of an APC, e.g., an APC presenting an alloantigen or an antigen peptide bound to an MHC molecule. Alternatively, if the activation is in vitro, the B7-H1 molecule can be bound to the floor of a the relevant culture vessel, e.g. a well of a plastic microtiter plate.

The methods can be performed in vitro, in vivo, or ex vivo. In vitro application of B7-H1 can be useful, for example, in basic scientific studies of immune mechanisms or for production of activated T cells for use in either studies on T cell function or, for example, passive immunotherapy. Furthermore, B7-H1 could be added to in vitro assays (e.g., in T cell proliferation assays) designed to test for immunity to an antigen of interest in a subject from which the T cells were obtained. Addition of B7-H1 to such assays would be expected to result in a more potent, and therefore more readily detectable, in vitro response. However, the methods of the invention will preferably be in vivo or ex vivo (see below).

The B7-H1 proteins and variants thereof are generally useful as immune response-stimulating therapeutics. For example, the polypeptides of the invention can be used for treatment of disease conditions characterized by immunosuppression: e.g., cancer, AIDS or AIDS-related complex, other virally or environmentally-induced conditions, and certain congenital immune deficiencies. The compounds may also be employed to increase immune function that has been impaired by the use of radiotherapy of immunosuppressive drugs such as certain chemotherapeutic agents, and therefore are particularly useful when given in conjunction with such drugs or radiotherapy. In addition, in view of the ability of B7-H1 to co-stimulate the production of especially high levels of IL-10, B7-H1 molecules can be used to treat conditions involving cellular immune responses, e.g., inflammatory conditions, e.g., those induced by infectious agents such *Mycobacterium tuberculosis* or *M leprae*), or other pathologic cell-mediated responses such as those involved in autoimmune diseases (e.g., rheumatoid arthritis (RA), multiple sclerosis (MS), or insulin-dependent diabetes mellitus (IDDM)).

These methods of the invention can be applied to a wide range of species, e.g., humans, non-human primates, horses, cattle, pigs, sheep, goats, dogs, cats, rabbits, quinea pigs, hamsters, rats, and mice.

In Vivo Approaches

In one in vivo approach, the B7-H1 polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intraperitoneally, intrarcctally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01–100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding the B7-H1 polypeptide or functional fragment can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1–10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5μm and preferably larger than 20μm.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043–1053; Todd et al. (1993), *J. Exp. Med.* 177, 1663–1674; Penix et al. (1993), *J. Exp. Med.* 178, 1483–1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the B7-H1 polypeptide or functional fragment of interest with an initiator methionine and optionally a targeting sequence is operatively linked to a promoter or enhancer-promoter combination.

Short amino acid sequences can act as signals to direct proteins to specific intracellular compartments. For example, hydrophobic signal peptides (e.g., MAISGVPV-LGFFIIAVLMSAQESWA (SEQ ID NO:6)) are found at the amino terminus of proteins destined for the ER. While the sequence KFERQ (SEQ ID NO:7) (and other closely related sequences) is known to target intracellular polypeptides to lysosomes, other sequences (e.g., MDDQRDLISNNEQLP (SEQ ID NO:8) direct polypeptides to endosomes. In addition, the peptide sequence KDEL (SEQ ID NO:9) has been shown to act as a retention signal for the ER. Each of these signal peptides, or a combination thereof, can be used to traffic the B7-H1 polypeptides or functional fragments of the invention as desired. DNAs encoding the B7-H1 polypeptides or functional fragments containing targeting signals will be generated by PCR or other standard genetic engineering or synthetic techniques.

A promoter is a TRE composed of a region of a DNA molecule, typically within 100 basepairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result (e.g., an enhanced T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10_6$ to $10_{12}$ copies of the polynucleotide molecule. This dose can be repeatedly administered, as needed. Routes of administration can be any of those listed above.

Ex Vivo Approaches

Peripheral blood mononuclear cells (PBMC) can be withdrawn from the patient or a suitable donor and exposed ex vivo to an activating stimulus (see above) and a B7-H1 polypeptide or polypeptide fragment (whether in soluble form or attached to a sold support by standard methodologies). The PBMC containing highly activated T cells are then introduced into the same or a different patient.

An alternative ex vivo strategy can involve transfecting or transducing cells obtained from the subject with a polynucleotide encoding an B7-H1 polypeptide or functional fragment-encoding nucleic acid sequences described above. The transfected or transduced cells are then returned to the subject. While such cells would preferably be hemopoietic cells (e.g., bone marrow cells, macrophages, monocytes, dendritic cells, or B cells) they could also be any of a wide range of types including, without limitation, fibroblasts, , epithelial cells, endothelial cells, keratinocytes, or muscle cells in which they act as a source of the B7-H1 polypeptide or functional fragment for as long as they survive in the subject. The use of hemopoietic cells, that include the above APC, would be particular advantageous in that such cells would be expected to home to, among others, lymphoid tissue (e.g., lymph nodes or spleen) and thus the B7-H1 polypeptide or functional fragment would be produced in high concentration at the site where they exert their effect, i.e., enhancement of an immune response. In addition, if APC are used, the APC expressing the exogenous B7-H1 molecule can be the same APC that presents an alloantigen or antigenic peptide to the relevant T cell. The B7-H1 can be secreted by the APC or expressed on its surface. Prior to returning the recombinant APC to the patient, they can optionally be exposed to sources of antigens or antigenic peptides of interest, e.g., those of tumors, infectious microorganisms, or autoantigens. The same genetic constructs and trafficking sequences described for the in vivo approach can be used for this ex vivo strategy. Furthermore, tumor cells, preferably obtained from a patient, can be transfected or transformed by a vector encoding a B7-H1 polypeptide or functional fragment therof. The tumor cells, preferably treated with an agent (e.g., ionizing irradiation) that ablates their proliferative capacity, arc then returned to the patient where, due to their expression of the exogenous B7-H1 (on their cell surface or by secretion), they can stimulate enhanced tumoricidal T cell immune responses. It is understood that the tumor cells which, after transfection or transformation, are injected into the patient, can also have been originally obtained from an individual other than the patient.

The ex vivo methods include the steps of harvesting cells from a subject, culturing the cells, transducing them with an expression vector, and maintaining the cells under conditions suitable for expression of the B7-H1 polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient.

Methods of Screening for Compounds that Inhibit or Enhance Immune Responses.

The invention provides methods for testing compounds (small molecules or macromolecules) that inhibit or enhance an immune response. Such a method can involve, e.g., culturing a B7-H1 polypeptide of the invention (or a functional fragment thereof with T cells in the presence of a T cell stimulus (see above). The B7-H1 molecule can be in solution or membrane bound (e.g., expressed on the surface of the T cells) and it can be natural or recombinant. Compounds that inhibit the T cell response will likely be compounds that inhibit an immune response while those that enhance the T cell response will likely be compounds that enhance an immune response.

The invention also relates to using B7-H1 or functional fragments thereof to screen for immunomodulatory compounds that can interact with B7-H1. One of skill in the art would know how to use standard molecular modeling or other techniques to identify small molecules that would bind to T cell interactive sites of B7-H1. One such example is provided in Broughton (1997) Curr. Opin. Chem. Biol. 1, 392–398.

A candidate compound whose presence requires at least 1.5-fold (e.g., 2-fold, 4-fold, 6-fold, 10-fold, 150-fold, 1000-fold, 10,000-fold, or 100,000-fold) more B7-H1 in order to achieve a defined arbitrary level of T cell activation than in the absence of the compound can be useful for inhibiting an immune response. On the other hand, a candidate compound whose presence requires at least 1.5 fold (e.g., 2-fold, 4-fold, 6-fold, 10-fold, 100-fold, 1000-fold, 10,000 fold, or 100,000-fold) less B7-H1 to achieve a defined arbitrary level of T cell activation than in the absence of the compound can be useful for enhancing an immune response. Compounds capable of interfering with or modulating B7-H1 function are good candidates for immunosuppressive immunoregulatory agents, e.g., to modulate an autoimmune response or suppress allogeneic or xenogeneic graft rejection.

B7-H1 Antibodies

The invention features antibodies that bind to either or both of the B7-H1 polypeptides or fragments of such polypeptides. Such antibodies can be polyclonal antibodies present in the serum or plasma of animals (e.g., mice, rabbits, rats, guinea pigs, sheep, horses, goats, cows, or pigs) which have been immunized with the relevant B7-H1 polypeptide or peptide fragment using methods, and optionally adjuvants, known in the art. Such polyclonal antibodies can be isolated from serum or plasma by methods known in the art. Monoclonal antibodies that bind to the above polypeptides or fragments are also embodied by the invention. Methods of making and screening monoclonal antibodies are well known in the art.

Once the desired antibody-producing hybridoma has been selected and cloned, the resultant antibody can be produced in a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for B7-H1, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041–43; Liu et al. (1987) J. Immunol. 139, 3521–26; Sun et al. (1987) PNAS 84, 214–18; Nishimura et al. (1987) Canc. Res. 47, 999–1005; Wood et al. (1985) Nature 314, 446–49; Shaw et al. (1988) J. Natl. Cancer Inst. 80, 1553–59; Morrison, (1985) Science 229, 1202–07; Oi et al. (1986) BioTechniques 4, 214; Winter, U.S. Pat. No. 5,225,539; Jones et al. (1986) Nature 321, 552–25; Veroeyan et al. (1988) Science 239, 1534; and Beidler et al. (1988) J. Immunol. 141, 4053–60.

Also included within the scope of the invention are antibody fragments and derivatives which contain at least the functional portion of the antigen binding domain of an antibody that binds specifically to B7-H1 . Antibody fragments that contain the binding domain of the molecule can be generated by known techniques. For example, such fragments include, but are not limited to: F(ab')$_2$ fragments which can be produced by pepsin digestion of antibody molecules; Fab fragments which can be generated by reducing the disulfide bridges of F(ab')$_2$ fragments; and Fab fragments which can be generated by treating antibody molecules with papain and a reducing agent. See, e.g., National Institutes of Health, 1 Current Protocols In Immunology, Coligan et al., ed. 2.8, 2.10 (Wiley Interscience, 1991). Antibody fragments also include Fv (e.g., single chain Fv (scFv)) fragments, i.e., antibody products in which there are no constant region amino acid residues. Such fragments can be produced, for example, as described in U.S. Pat. No. 4,642,334 which is incorporated herein by reference in its entirety.

The following examples are meant to illustrate, not limit, the invention.

EXAMPLE 1

Materials and Methods

Cloning of hB7-H1 cDNA and construction of Ig fusion proteins. The 5' and 3' ends of hB7-H1 cDNA were amplified by PCR from a human placenta cDNA library synthesized by SMART PCR cDNA synthesis kit (Clontech, Palo Alto, Calif.). The primer pairs used for the PCR were derived from the placenta library plasmid and from the expressed sequence tag (EST) clone AA292201. A cDNA clone that included an orf encoding hB7-H1 of hB7-H1 cDNA was amplified by PCR from the same cDNA library by specific primers and cloned into the pcDNA3 vector (Invitrogen, Carlsbad, Calif.) and sequenced. The amino acid sequences of hB7-H1, B7-1 and B7-2 were analyzed using the ClustalW algorithm with BLOSUM 30 matrix (MacVector, Oxford Molecular Group). The hB7-H1Ig fusion protein was prepared by fusing the extracellular domain of hB7H-1 to the CH2-CH3 domain of mouse IgG2a in the expression plasmid pmIgv and the resulting construct was transfected into CHO cells. An identical method was also used for preparation of B7-1Ig. CTLA4Ig, and ICOSIg fusion proteins. The fusion proteins were purified from culture supernatants by passage over a Protein G -Sepharose affinity columns (Pharmacia, Uppsala, Sweden) and the purified fusion proteins were dialyzed into endotoxin-free PBS.

DNA transfection. Plasmids containing nucleic acid sequences encoding full length hB7-H1 (pcDNA3-hB7-H1), B7-1 (pCDM8-B7.1) or control parental vectors without coding sequences were transfected into 293 cells or COS cells by calcium phosphate or DEAE-Dextran transfection (Promega, Madison, Wis.). After 48 hours of incubation, the expression levels of hB7-H1 or B7-1 on transfectants were determined by FACS analysis with an antiserum specific for hB7-H1 or anti-B7-1 monoclonal antibody (mAb) (PharMingen), respectively.

T-cell and cytokine assays. PBMC were isolated from the blood of healthy human volunteer donors by Ficoll-Hypaque gradient centrifugation. The PBMC were passed through a nylon wool column to obtain purified T cells (~85% of CD3$^+$cells), or were subjected to further purification (>95% of CD3$^+$cells) using an anti-CD4/8 MACS magnetic bead system (Miltenyl Biotec, Germany). For co-stimulation assays, purified T cells at a concentration of $1 \times 10^5$ cells/well were cultured in triplicate in 96-well flat-bottomed microtiter tissue culture plates that were pre-coated overnight with antibody specific for human CD3 (HIT3a, PharMingen, Palo Alto, Calif.) and either hB7-H1 Ig (5 µg/ml) or control Ig (purified mouse IgG2a or murine 4-1 BBIg fusion protein). In some experiments, the microtiter wells were coated with only antibody specific for CD3 and B7-1- or hB7-H1- transfected COS cells were used ($10^4$ cells/well) as a source of the co-stimulatory molecules. To measure cytokine production, supernatants were collected at 24, 48 and 72 hours after initiation of the cultures and the concentrations of IL-2, IL-4, IFN-γ and IL-10 were determined by sandwich ELISA (PharMingen) according to the manufacturer's instructions. Wells containing B7-1Ig or antibody specific for human CD28 (CD28.2. PharMingen) were included for comparison or as a positive control, respectively. T cell proliferation was determined by the addition of 1.0 µCi [$^3$H]-thymidine per well on day 2 followed by at least 18 hours of additional culture. Incorporated [$^3$H]-thymidine was determined using a MicroBeta TriLux liquid scintillation counter (Wallac, Finland).

For mixed lymphocyte reaction (MLR) assays, purified T cells ($2 \times 10^5$ cells/well) were co-cultured in triplicate with allogeneic PBMC (4000 Rad-irradiated) at $2 \times 10^5$ cells/well in the presence of soluble hB7-H1Ig or control Ig. Four days later, T cell proliferation was determined by [$^3$H]-thymidine incorporation. Neutralizing mAb specific for human IL-2 (Clone MQ1-17H12, PharMingen) was added at 8 µg/ml in the beginning of T cell cultures. Polymyxin B at 10 µg/ml was also included in the assays of cell proliferation and cytokine secretion to completely neutralize any contaminating endotoxin.

Nucleic acid analysis. Northern blot analysis was carried out using commercially available human multiple tissue Northern blots (Clontech, Palo Alto, Calif.). The membrane was incubated in ExpressHyb hybridization solution (Clontech) for 30 min at 68° C. The random-primed cDNA probe was full length hB7-H1 coding cDNA (870 bp), and was labeled using $^{32}$P-dCTP. The human β-actin cDNA probe (2.0 kb) was used as a control. Hybridization was carried out for 1 hr at 68° C., the membrane was washed 3times in 2×SSC containing 0.05% SDS, and was then exposed at−70° C. to x-ray film.

Flow cytometry analysis. To prepare an antiserum specific for hB7-H1, mice were immunized with purified hB7-H1Ig emulsified in complete Freund's adjuvant (Sigma) and boosted three times with hB7-H1Ig in incomplete Freund's adjuvant. Serum was collected and the specificity was determined by ELISA and by FACS staining (1:1000 dilution) of hB7-H1 cDNA-transfected 293 cells or COS cells. Preinjection mouse serum was used as control.

To prepare activated T and B cells, freshly isolated human PBMC ($10 \times 10^6$ cells/ml) were activated with 5 µg/ml of PHA (Sigma) or 10 µg/ml of LPS (Sigma), respectively. For preparation of activated monocytes, adherent PBMCs were cultured in 1,500 IU/ml of recombinant human IFN-γ (Biosource, Camarillo, Calif.) and 100 ng/ml of LPS. All cultures were harvested and analyzed at 48 hours. For direct immunofluorescence staining, T cells were incubated at 4° C. with 1 µg of either fluorescein- (FITC) or phycoerythrin- (PE) conjugated mAb for 30 min and analyzed by FACScan flow cytometry (Becton Dickinson, Mountain View, Calif.) with Cell Quest software (Becton Dickinson) as described previously. The mAb specific for CD3 (UCHT1), CD4 (RPA-T4), CD8 (RPA-T8), CD14 (M5E2), CD19 (B43), CD28 (CD28.2), CD80 (BB1) were purchased from PharMingen. For indirect immunofluorescence staining, cells were first incubated with anti-hB7-H1 antibody (1:1000), 5 µg of ICOSIg or CTLA4Ig at 4° C. After 30 min, the cells were washed and further incubated with FITC- (Biosource, Camarillo, Calif.) or PE-conjugated (Southern Biotechnology Associates, Inc., Birmingham, Ala.) goat anti-human or anti-mouse IgG F(ab')$_2$ for 30 min at 4° C. The human or mouse IgG1 protein (Sigma) or mouse 4-1BBIg (mouse 4-1BB extracellular domain fused with the Fc of human IgG1 or mouse IgG2a) was used as control Ig. In some experiments, Fc receptors were blocked by human or mouse Ig before incubation with FITC- or PE-conjugated mAbs.

EXAMPLE 2

Molecular Cloning and Expression Pattern of the hB7-H1 gene

A homology search of the human cDNA EST database using published human B7-1 and B7-2 amino acid sequences revealed an EST sequence (GeneBank #AA292201) encoding a homologue to human B7-1 and B7-2 molecules. The 5'- and 3'- sequences were obtained by several independent reverse transcriptase-coupled polymerase chain reactions (RT-PCR) from a human placenta cDNA library utilizing vector and EST sequences as primers. A 3,616 bp fragment that included the hB7-H1 encoding orf was cloned and sequenced (SEQ ID NO:5) (FIG. 1). The coding sequence for hB7-H1 (SEQ ID NO:2) spans nucleotides 73-942 of SEQ ID NO:5. The amino acid sequence of full-length hB7-H1 (SEQ ID NO:1) is shown in FIG. 2a. The extracellular domain of hB7-H1 has greater homology to B7-1 (20% amino acid identity) than to B7-2 (15%) (FIG. 2b) whereas its cytoplasmic domain is highly divergent from that of B7-1 and B7-2 based on analysis using the McVector 6.5 software. The open reading frame of the gene encodes a type I transmembrane protein of 290 amino acids consisting of a 22 amino acid signal peptide, Ig V-like domain, and Ig C-like domains, a hydrophobic transmembrane domain and a cytoplasmic tail of 30 amino acids (FIG. 2a). Four structural cysteines (labeled by stars in FIG. 2b), which are apparently involved in forming the disulfide bonds of the Ig V and Ig C domains are well conserved in all B7 members (FIG. 2b) [Fargeas, Calif. et al. (1995) *J. Exp. Med.* 182, 667–675; Bajorath, J. et al. (1994) *Protein Sci.* 3, 2148–50; Linsley, P. S. et al. (1994) *Immunity* 1, 793–801; Inaba, K. et al. (1994) *J. Exp. Med.* 180, 1849–60; Freeman, G. J. et al. (1995) *Immunity* 2, 523–532]. In addition, the tyrosine residue in B7-1 (at position 87) and in B7-2 (at position 82) of the Ig V-like domain is conserved in hB7-H1 (at position 81) (FIG. 2b).

Northern blot analysis revealed that expression of the hB7-H1 mRNA was abundant in heart, skeletal muscle, placenta and lung but was weak in thymus, spleen, kidney and liver (FIG. 3). The hB7-H1 mRNA was not detectable in brain, colon, small intestine and peripheral blood mononuclear cells (PBMC). In most of the tissues in which hB7-H1 mRNA was detectable, two transcripts of approximately 4.1 and 7.2 kb were found.

Figure 4A:
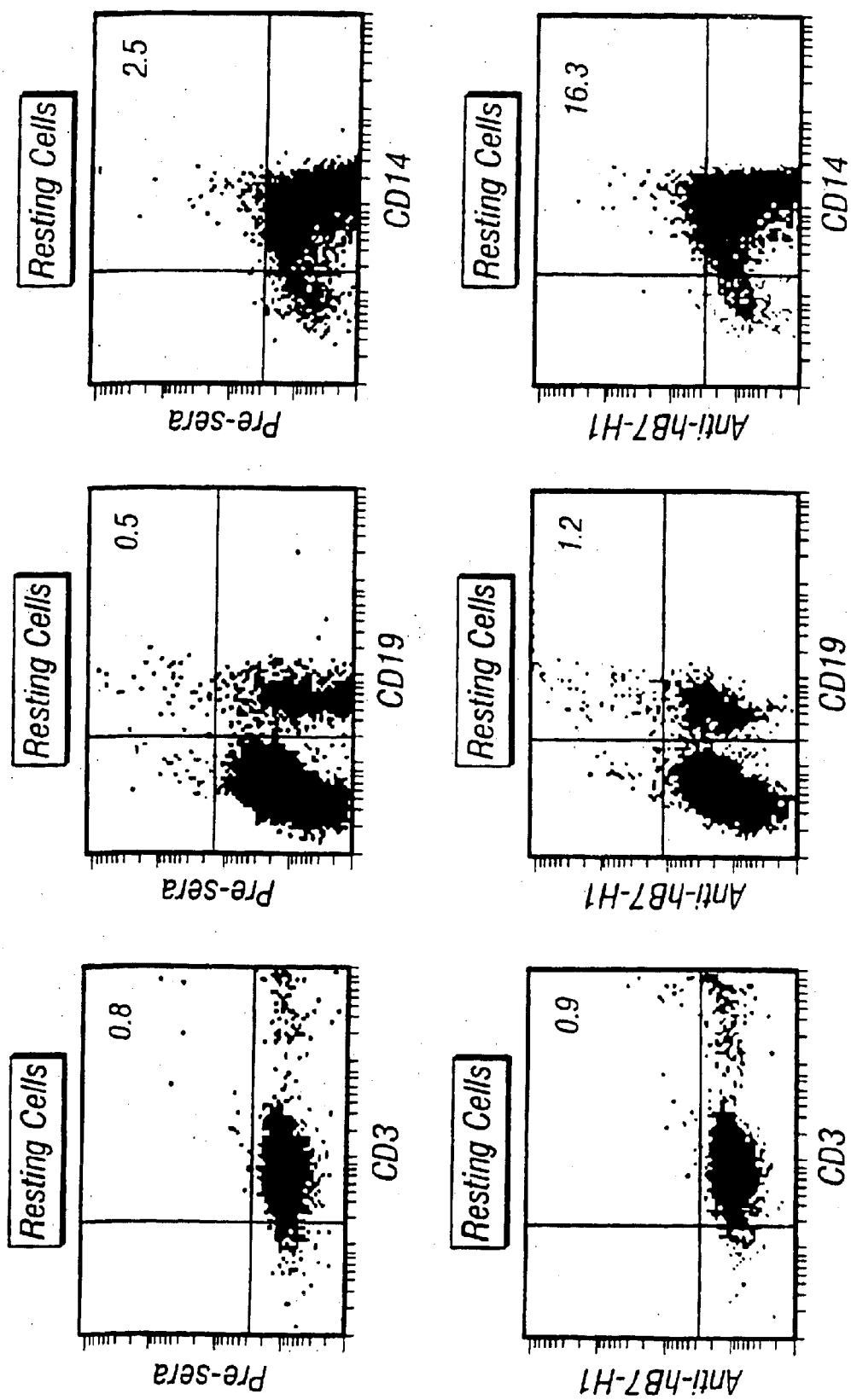
FIG. 4 is a series of two-dimensional fluorescence flow cytometry histograms showing cell surface expression of hB7-H1 on resting and activated CD3+T cells, CD19+B cells, and CD14+monocytes.
Figure 4B:
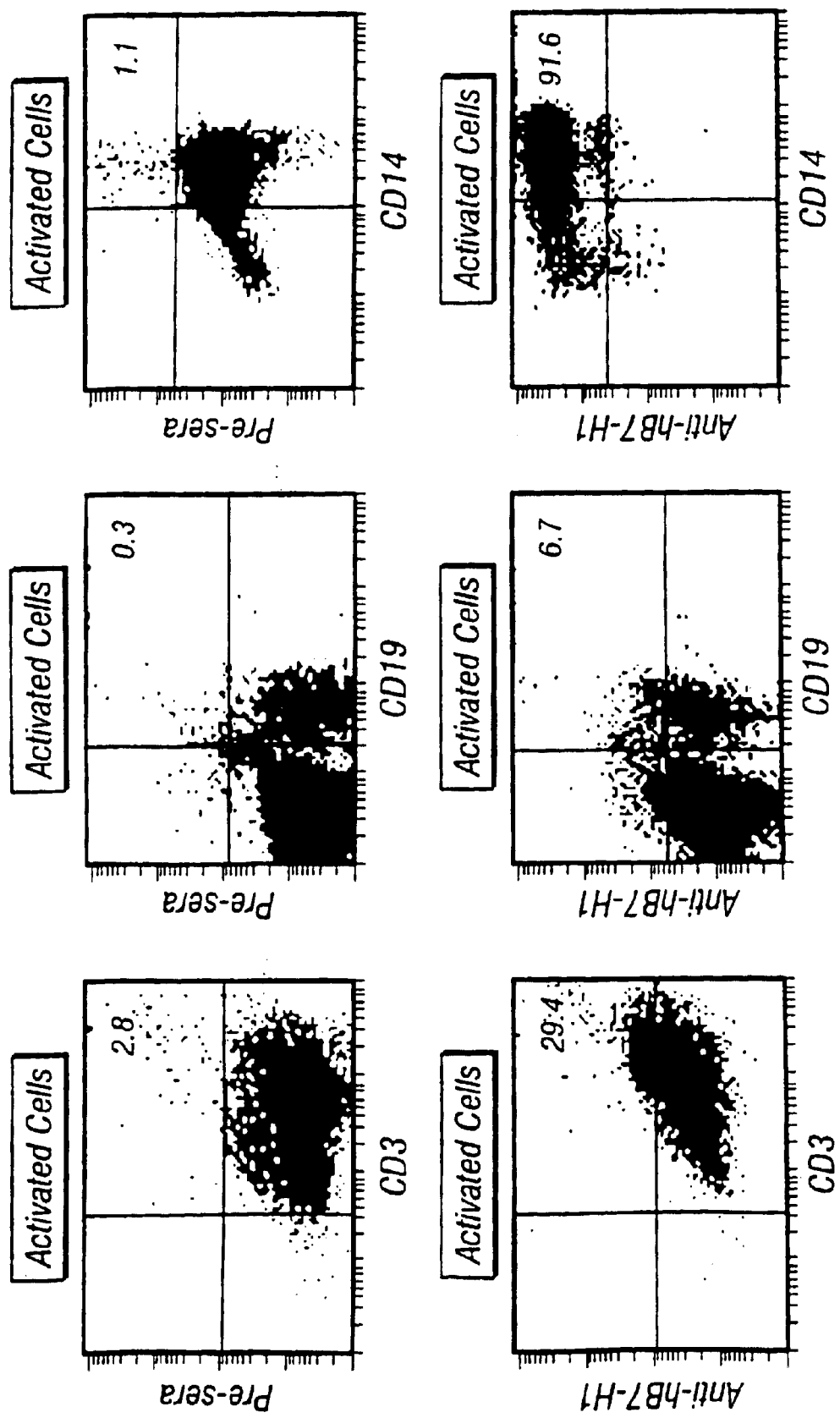

An expression plasmid containing the extracellular domain of hB7-H1 fused in frame with the Fc portion (CH2 and CH3-domains) of the mouse IgG2a was constructed. The resulting product, hB7-H1Ig fusion protein, was purified from the supernatants of CHO cells transfected with the plasmid and was used for immunization of the mice to prepare a hB7-H1 -specific antiserum. Fluorescence flow cytometry analysis using the hB7-H1-specific antiserum showed that freshly isolated CD3+T and CD19+B cells express negligible levels of hB7-H1 while a fraction (~16%) of CD14+monocytes constitutively express hB7-H1. HB7-H1 can, however, be up-regulated by cell activation. Approximately 30% of PHA-treated CD3+T cells and 90% of CD14+monocytes (treated with IFN-γ and LPS) express hB7-H1 . Only 6% of CD19+B cells after LPS activation express hB7-H1 (FIG. 4). Confirmatory results were obtained by RT-PCR analysis.

Figure 5A:
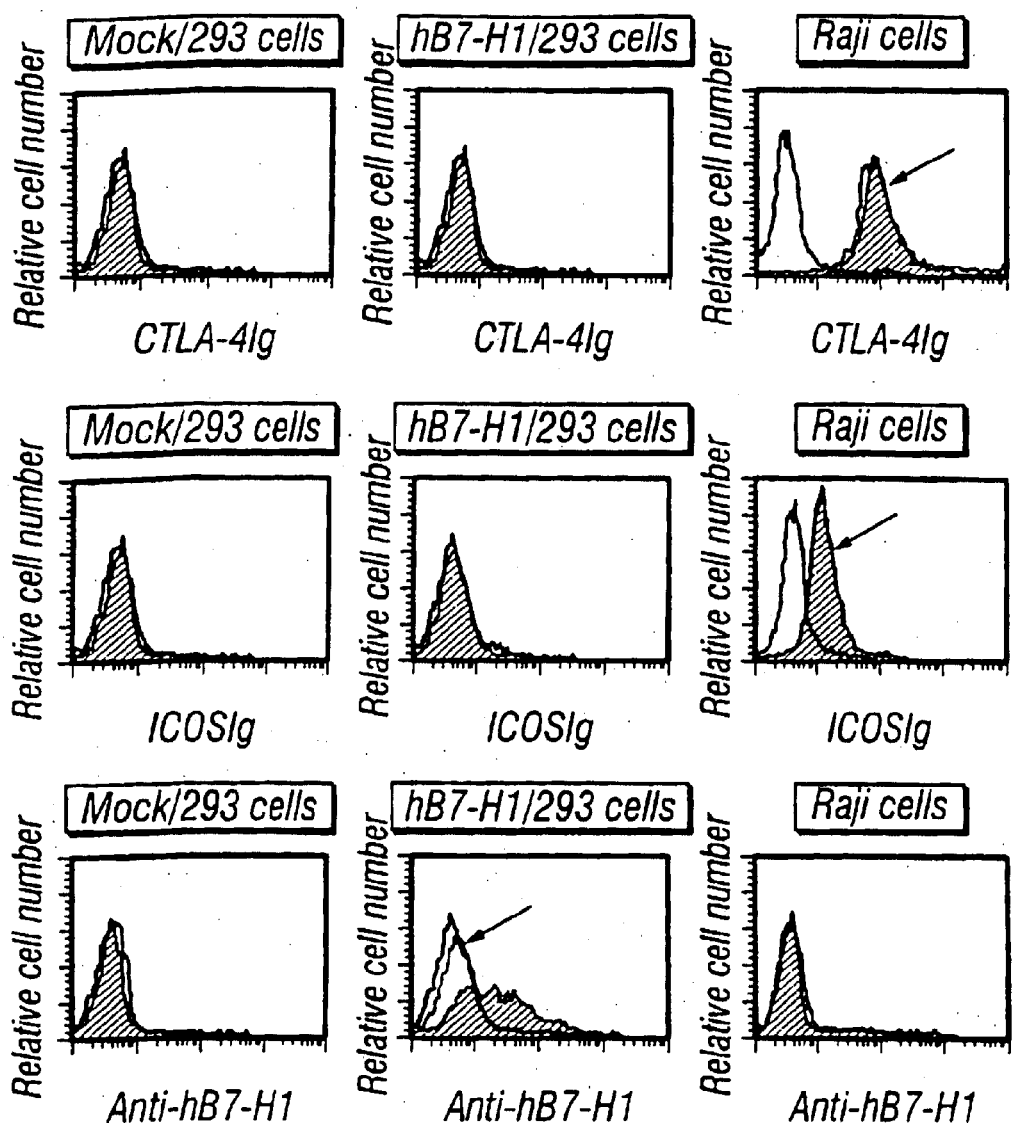
FIG. 5a is a series of fluorescence flow cytometry histograms showing binding of CTLA-4Ig, ICOSIg, and antibody specific for hB7-H1 to 293 cells transfected with either a control vector (Mock/293 cells) or a vector containing a cDNA insert encoding hB7-H1 (B7-H1/293 cells), or Raji cells.
Figure 5B:
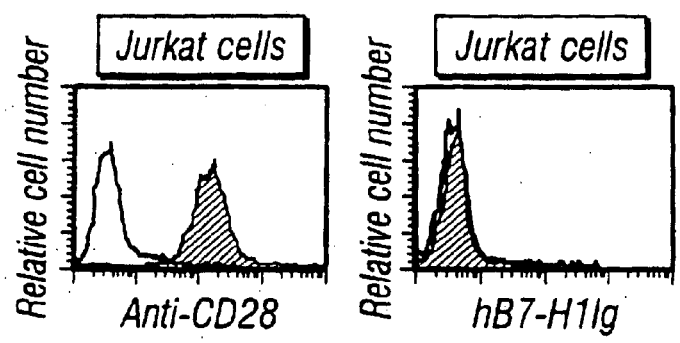
FIG. 5b is a series of fluorescence flow cytometry histograms showing the binding of mB7-H1Ig and antibody to CD28 to Jurkat cells.

Transfection of the plasmid pcDNA3-hB7-H1 into 293 cells (B7-H1/293 cells) led to the expression of hB7-H1 as detected by hB7-H1-specific antiserum (FIG. 5a). The binding of antibody was eliminated by the inclusion of soluble hB7-H1Ig in the staining mixture (FIG. 5a, arrow), thereby demonstrating specificity of the antiserum. Neither CTLA4Ig nor ICOSIg bound to hB7-H1/293 cells. Although both CTLA4Ig and ICOSIg bound to Raji cells, the binding was not blocked by the inclusion of hB7-H1Ig (FIG. 5a, arrows). Taken together with the observation that hB7-H1Ig did not bind to Jurkat cells (FIG. 5b, right panel), despite their constitutive expression of CD28 (FIG. 5b, left panel), the above results indicate that hB7-H1 is not a ligand for CD28, CTLA-4, or ICOS.

EXAMPLE 3

Co-stimulation of T Cell Proliferation by hB7-H1 ligation

Figure 6A:
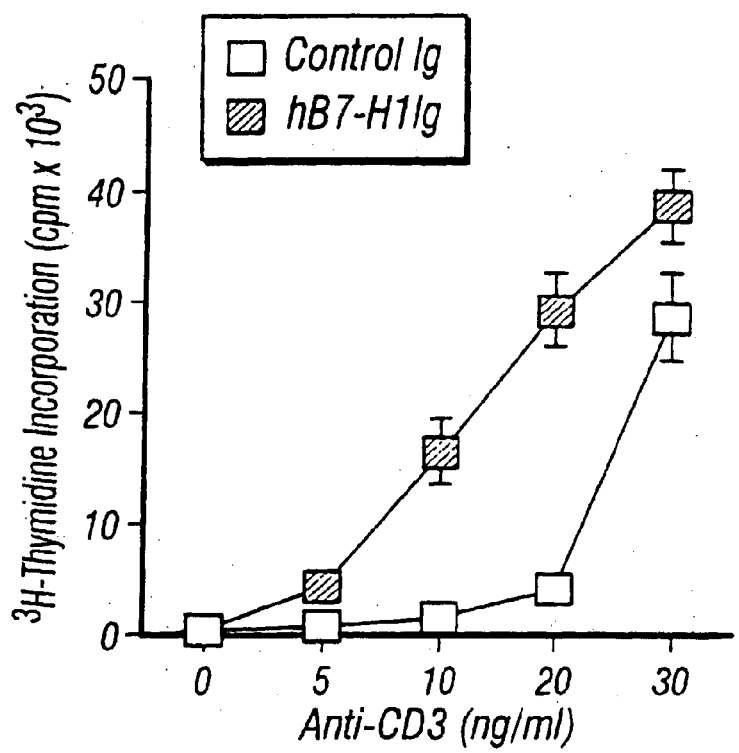
FIG. 6a is a line graph showing the ability of immobilized hB7-H1 to co-stimulate the proliferative response of human T cells to immobilized antibody specific for human CD3.
Figure 6B:
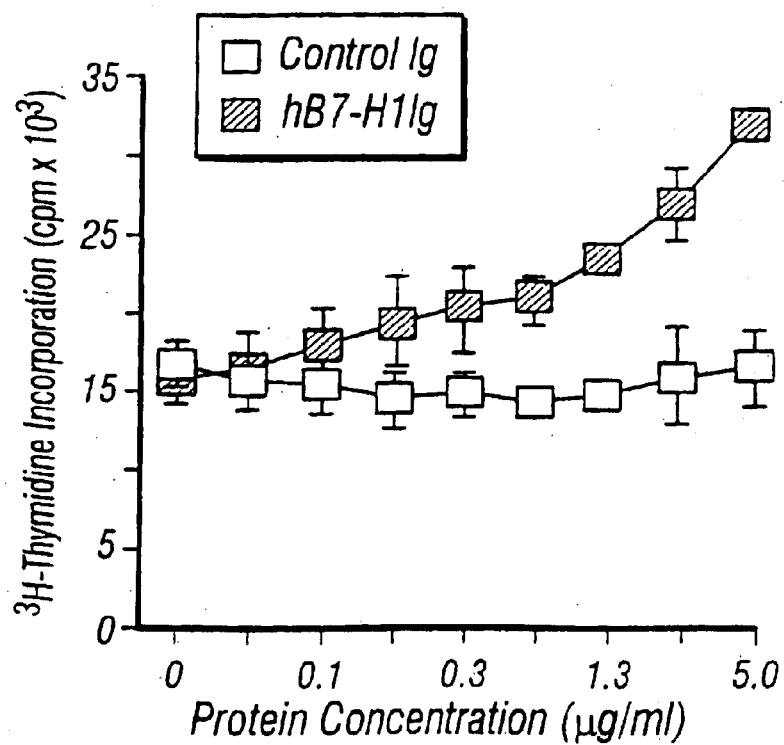
FIG. 6b is a line graph showing the ability of soluble hB7-H1 to co-stimulate the proliferative response of human T cells to irradiated allogeneic PBMC.

To assess whether hB7-H1 co-stimulates T-cell growth, T cells purified (>95% purity) from PBMC of healthy human donors were stimulated with hB7-H1Ig in the presence of suboptimal doses of anti-CD3 mAb. T cell proliferation in 3-day cultures was determined by incorporation of [$^3$H]-thymidine. hB7-H1Ig, immobilized on culture plates, enhanced T cell proliferation up to 10-fold compared to the control Ig in the presence of 5–20 µg/ml of anti-CD3 mAb, also immobilized on the culture plates. In the absence of anti-CD3 antibody, hB7-H1Ig at a concentration up to 5 µg/ml induced no T cell proliferation (FIG. 6a). If hB7-H1Ig was included in the cultures without immobilization, its co-stimulatory effect was significantly decreased. Consistent with this observation, the inclusion of soluble hB7-H1Ig at levels of 0.6-5 µg/ml in allogeneic MLR moderately (2-fold) increased the proliferation of T cells (FIG. 6b). Thus, hB7-H1 can promote and co-stimulate proliferative responses of T cells to polyclonal T cell stimuli and to allogeneic antigens.

EXAMPLE 4 hB7-H1 Co-stimulation Preferentially Induces the Production of IL-10 and the Co-stimulatory Effect Requires IL-2

Figure 7D:
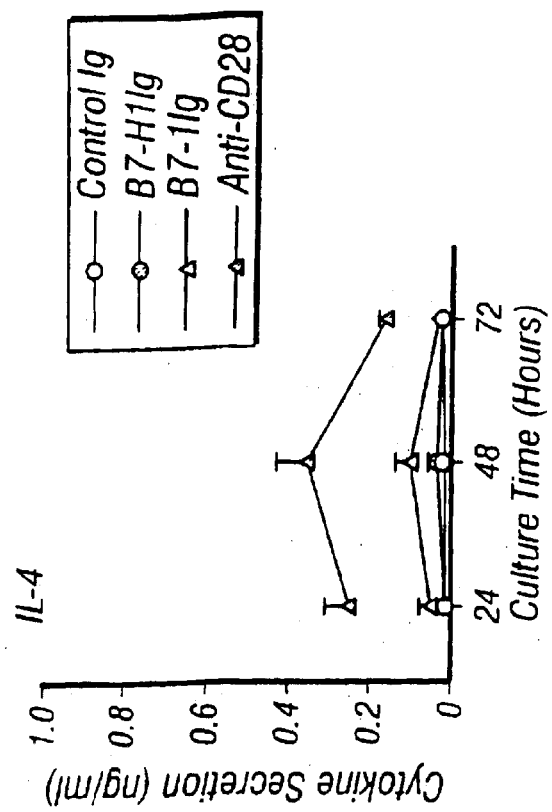
FIGS. 7a–7d are a series of line graphs showing the ability of hB7-H1Ig, or antibody specific for CD28 to co-stimulate the production by human T cells responding to immobilized antibody specific for CD3 of IL-10 (FIG. 7a), IFN-γ (FIG. 7b), IL-2 (FIG. 7c), IL-4 (FIG. 7d).
Figure 7C:
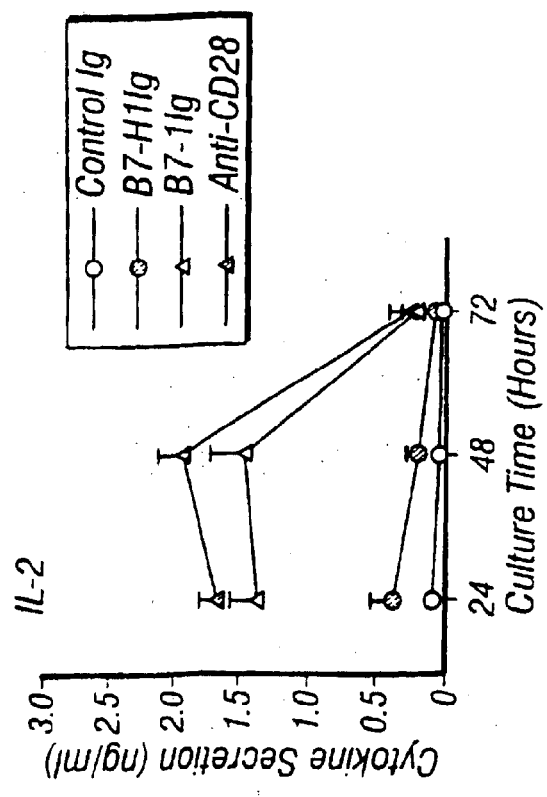

The levels of IL-2, IL-4, IFN-γ, and IL-10 produced by T cells after co-stimulation with hB7-H1Ig, B7-1Ig, or anti-CD28 mAb in the presence of anti-CD3 (FIGS. 7a–7d) were measured. Similar to B7-1Ig and anti-CD28, immobilized hB7-H1Ig antibody dramatically increased the production of IL-10 by T cells in response to immobilized anti-CD3 antibody after stimulation for 48 and 72 hours (FIG. 7a). IL-10 was not detected if T cells were co-stimulated with immobilized control Ig. The level of IFN-γ was also significantly elevated by co-stimulation with immobilized hB7-H1Ig (FIG. 7b). In contrast to B7-1Ig and anti-CD28, hB7-H1Ig co-stimulated low or negligible levels of IL-2 (FIG. 7c) and IL4 (FIG. 7d), respectively. These observations were reproducible in six independent experiments. These results show that co-stimulation by hB7-H1 preferentially stimulates the production of IL-10.

Figure 7E:
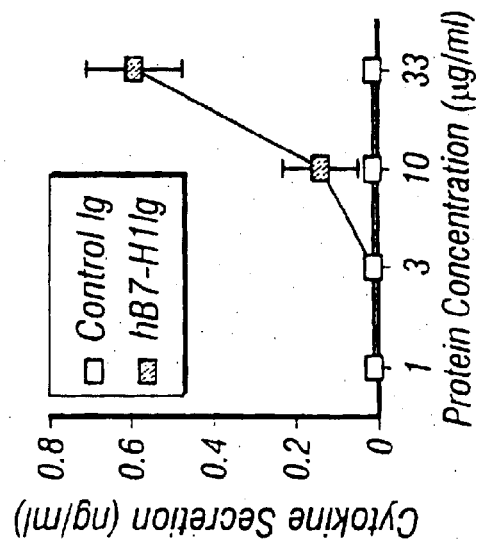
Figure 8A:
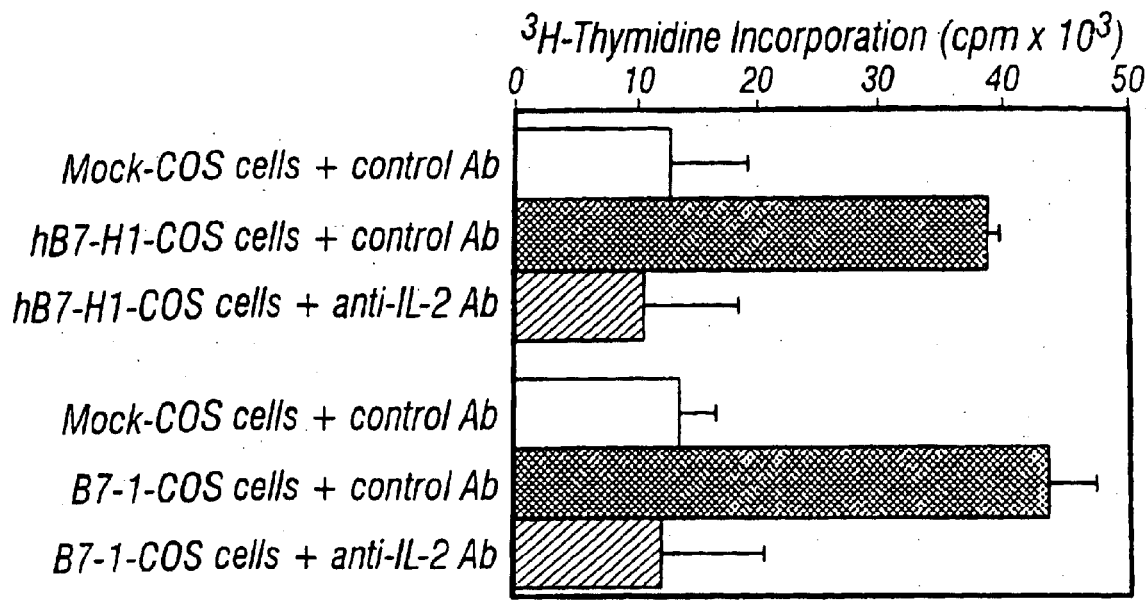
FIG. 8a is a bar graph showing the ability of antibody specific for IL-2 to inhibit the proliferation of human T cells induced by antibody specific for human CD3 and co-stimulated by COS cells transfected with and expressing either hB7-H1 or B7-1.
Figure 8B:
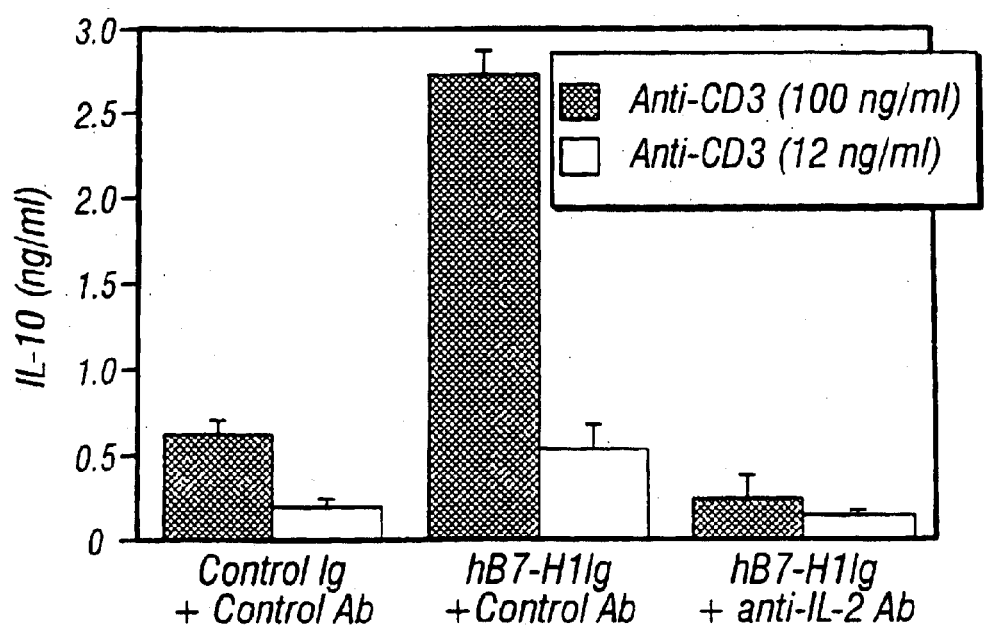
FIG. 8b is a bar graph showing the ability of antibody specific for IL-2 to inhibit the production of IL-10 by human T cells stimulated by immobilized antibody specific for human CD3 and co-stimulated by either hB7-H1Ig or B7-1Ig.

The production of IL-2, although low, peaked at 24 hours upon hB7-H1 co-stimulation (FIG. 7c), while IL-10 secretion started to increase only after 48 and 72 hours (FIG. 7a). Increasing concentrations of hB7-H1Ig led to a small increase (<1 ng/ml) of IL-2 secretion (FIG. 7e). To determine the roles of the early-produced IL-2, the effects of anti-IL-2 mAb on T cell proliferation and IL-10 production in B7H-mediated co-stimulation were tested. Similar to proliferation induced by B7-1-COS cells and immobilized anti-CD3 antibody T cell proliferation induced by hB7-H1-COS cells and anti-CD3 antibody was blocked by inclusion of anti-IL-2 mAb (FIG. 8a). Furthermore, IL-10 secretion from hB7-H1Ig-co-stimulated T cells was also inhibited by anti-IL-2 nab (FIG. 8b). Therefore, the hB7-H1 co-stimulation of both T cell growth and IL-10 secretion is an IL-2-dependent process.

EXAMPLE 5 hB7-H1 Co-stimulation Increases Apoptosis of Activated T Cells.

Figure 9A:
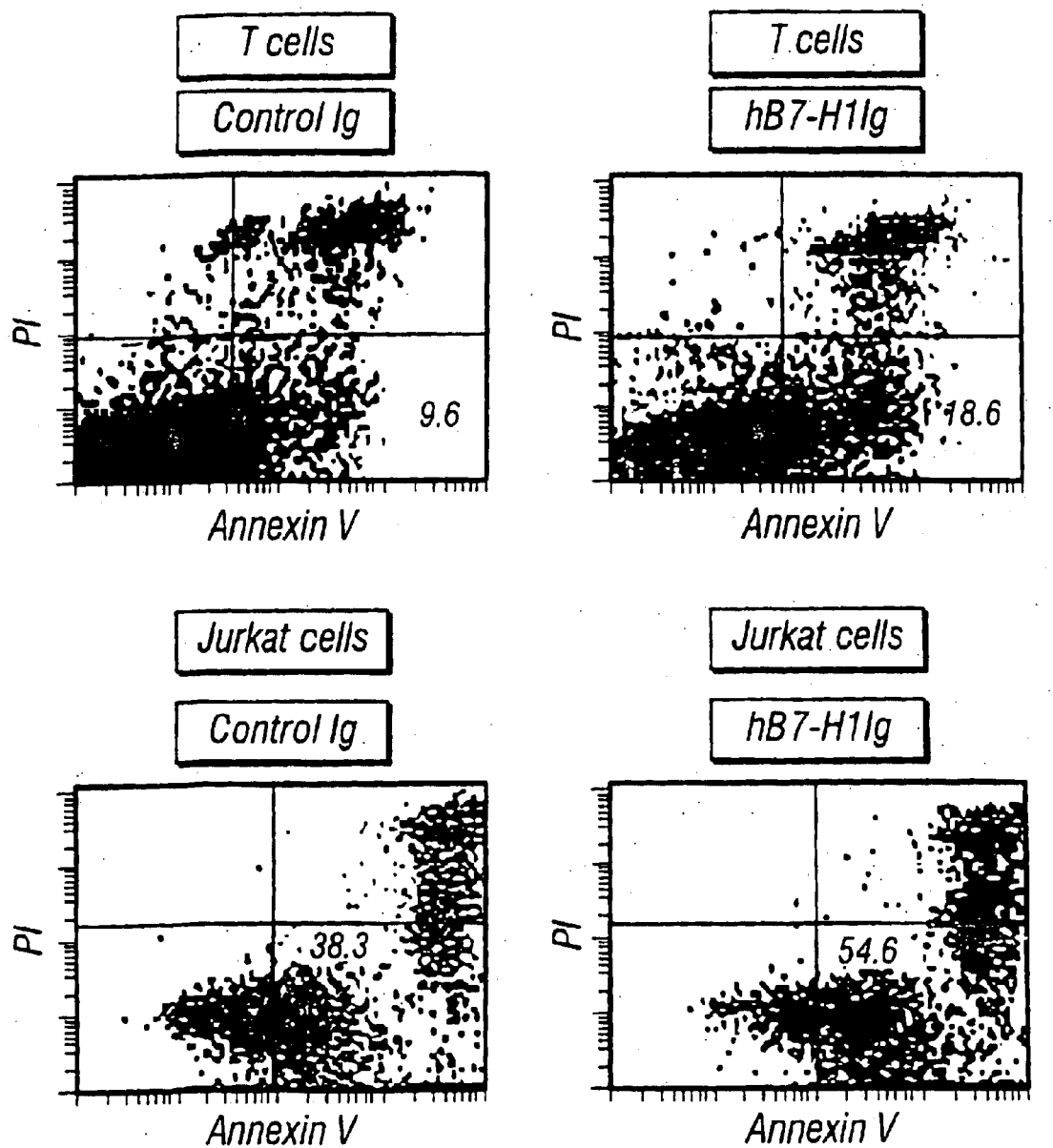
FIG. 9a is a series of two-dimensional fluorescence flow cytometry profiles showing the relative proportion of T cells in the early (annexin V-positive, propidium iodide (PI)-negative) and late (annexin V-positive, PI-positive) apoptosis following activation by immobilized antibody specific for human CD3 and co-stimulation with either control Ig or hB7-H1Ig.
Figure 9B:
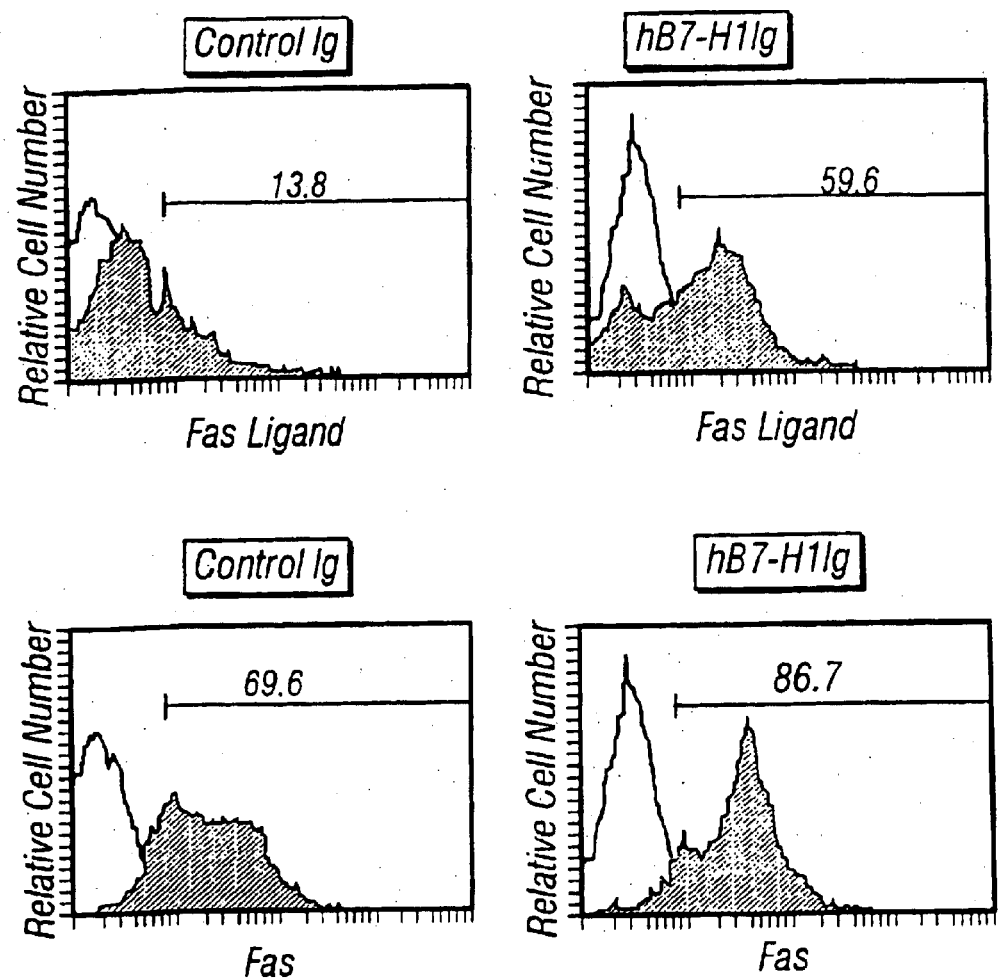
FIG. 9b is series of fluorescence flow cytometry profiles showing expression of Fas and FasL on human T cells following activation by immobilized antibody specific for human CD3 and co-stimulation with either control Ig or hB7-H1Ig.

To determine the effect of hB7-H1 ligation on the viability of activated T cells, the proportion of live T cells remaining after activation with an optimally activating dose of anti-CD3 antibody in the presence of immobilized hB7-H1Ig was determined by trypan blue staining. A consistent decrease of alive T cells was observed. At the end of culture, T cells were stained with annexin V and propidium iodide (PI) to distinguish the early phase and late phase of apoptosis, respectively. The apoptotic cells in early phase (annexin V-positive, PI-negative) were significantly increased to 24.8% in the presence of hB7-H1Ig compared to 14.2% in the absence of hB7-H1Ig in 5 experiments (P=0.001). A representative experiment is shown in FIG. 9a (upper panel). Similar results were obtained using hB7-H1Ig-treated Jurkat cells (control Ig: 38.3% vs. hB7-H1Ig: 54.6%) (FIG. 9a, lower panel). The increased apoptosis was associated with upregulation of Fas and FasL expression on hB7-H1 co-stimulated T cells (FIG. 9b). These results indicated that hB7-H1 co-stimulation increased activation-induced T cell apoptosis moderately, and the increased apoptosis was associated with elevated expression of Fas and FasL.

EXAMPLE 6

Production of Monoclonal Antibodies Specific for hB7-H1.

Using standard protocols, BALB/c mice were immunized with purified hB7-H1Ig and splenocytes from the immunized mice were fused with X63-AG8.653 mouse myeloma cells. Five hybridoma lines were found to secrete antibodies specific for hB7-H1 in that, as detected by fluorescence flow cytometry, culture supernatants from these hybridoma lines positively stained hB7-H1/293 cells but did not stain control vector/293 cells. Furthermore, some of the antibodies inhibited the co-stimulatory activity of hB7-H1.

EXAMPLE 7

Molecular Cloning and Expression Pattern of a Mouse B7-H1 (mB7-H1) Gene

Starting with two overlapping mouse EST clones (AA823166 and AA896104), and using a strategy similar to that for the hB7-H1 gene, a cDNA fragment that included an orf encoding mB7-H1 was cloned. The coding sequence for mB7-H1 (SEQ ID NO:4) (FIG. 10) was obtained and the amino acid sequence of mB7-H1 (SEQ ID NO: 3) (FIG. 11) was derived from it. The length of mB7-H1 is identical to that of hB7-H1 and it has the same conserved cysteine residues found in hB7-H1 (see Example 2).

As for hB7-H1, mB7-H1 was found to be expressed on very few B cells but on a high proportion of macrophages. The proportion of expressing macrophages was similarly increased by activation. Also like hB7-H1, mB7-H1 co-stimulated mouse T cell proliferation, as well as the production of IL-10, IFN-γ, and low levels of IL-2.

EXAMPLE 8

Expression of mB7-H1 on Transfected P815 Tumor Cells and Decreased Growth Rate of the Transfected P815 Cells in Mice.

Figure 12A:
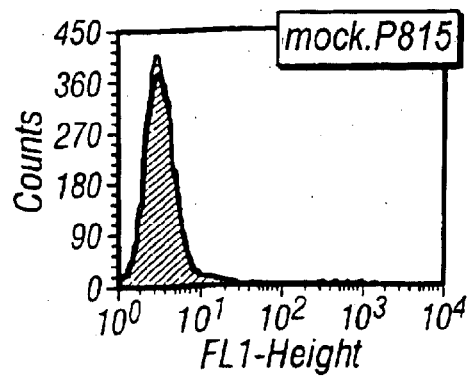
FIG. 12a and FIG. 12b are fluorescence flow cytometry histograms showing lack of surface expression of murine B7-1 (FIG. 12a) and mB7-H1 (FIG. 12b) on P815 cells transfected with a control expression vector.
Figure 12B:
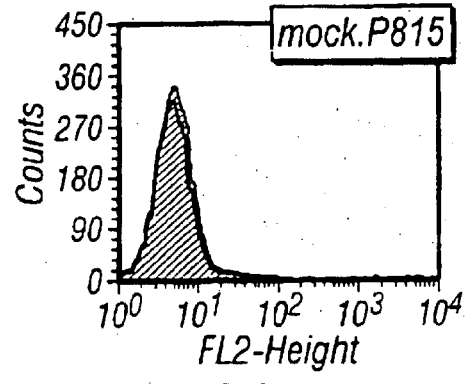
Figure 13A:
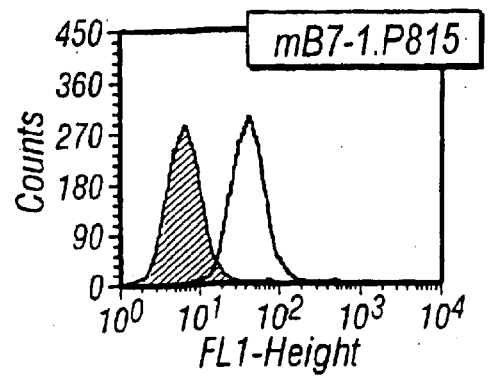
FIG. 13a and FIG. 13b are fluorescence flow cytometry histograms showing surface expression of murine B7-1 (FIG. 13a) and lack of surface expression of mB7-H1 (FIG. 13b) on P815 cells transfected with an expression vector containing a nucleic acid sequence encoding murine B7-1.
Figure 13B:
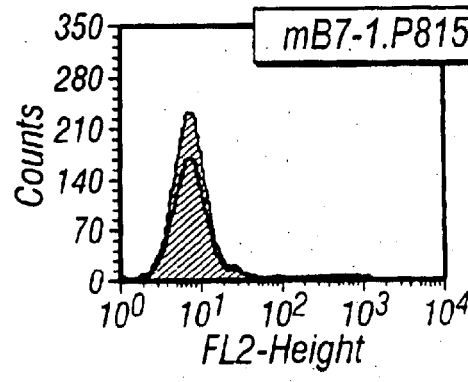
Figure 14A:
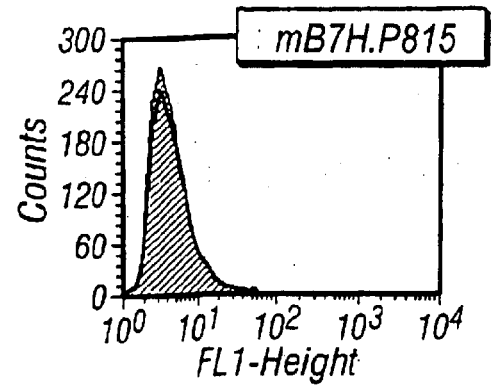
FIG. 14a and FIG. 14b are fluorescence flow cytometry histograms showing lack of surface expression of murine B7-1 (FIG. 14a) and surface expression of mB7-H1 (FIG. 14b) on P815 cells transfected with an expression vector containing a nucleic acid sequence encoding mB7-H1.
Figure 14B:
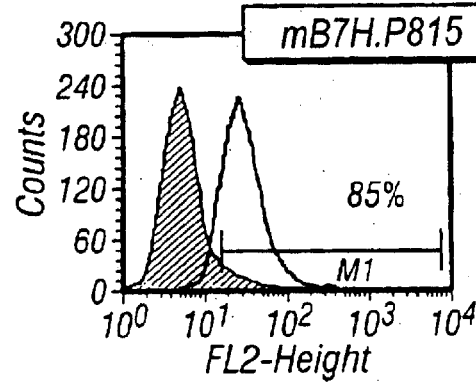

Mouse (DBA/2) P815 mastocytoma cells were stably transfected with a construct containing the coding sequence for mB7-H1 (mB7H.P815 cells). Using a PE-conjugated rat polyclonal antibody specific for mB7-H1 (anti-mB7H/PE), mB7-H1 expression was detected fluorescence flow cytometry on the mB7H.P815 cells (FIG. 14b) but not on either mock transfected P815 cells (mock.P815) (FIG. 12b) or P815 cells transfected with a construct encoding murine B7-1 (mB7-1.P815) (FIG. 13b). On the other hand, the mB7-1.P815 cells were stained with a FITC-conjugated mAb specific for murine B7-1 (anti-mB7-1 -FITC) (FIG. 13a).

Figure 15B:
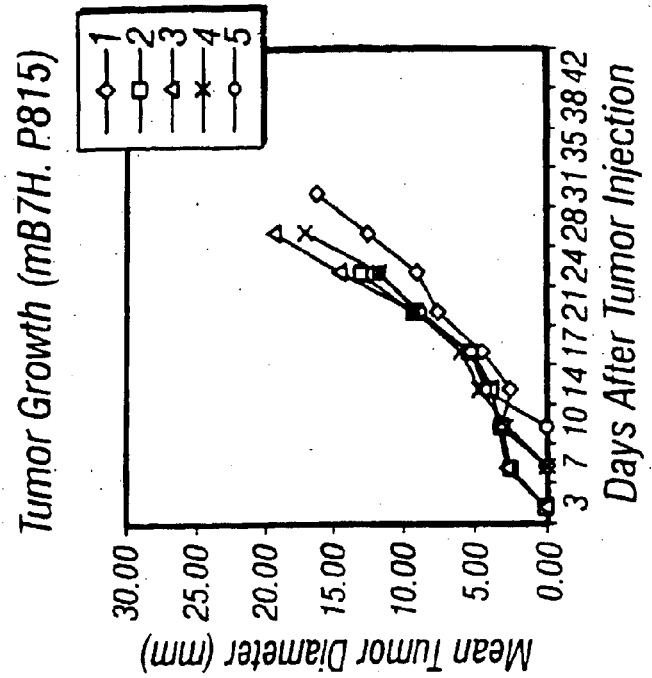
FIG. 15a and FIG. 15b are line graphs showing the growth rate of P815 tumors in DBA/2 mice injected subcutaneously with P815 cells transfected with a control expression vector (FIG. 15a) or an expression vector containing a nucleic acid sequence encoding mB7-H1.
Figure 15A:
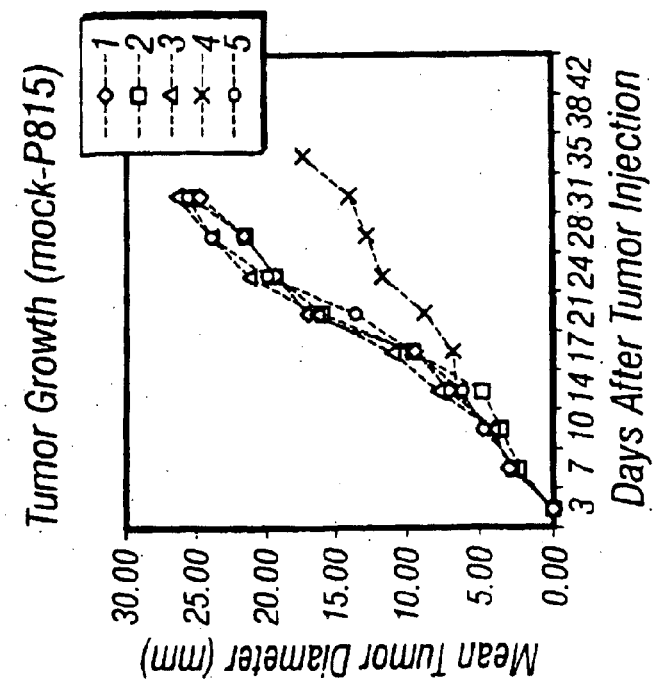

Groups (5 mice per group) of DBA/2 mice were injected subcutaneously (s.c.) with either $2\times10^5$ mock.P815 or mB7-1.P815 cells. The growth rate of the mock.P815 cells was significantly greater in 4 out of 5 injected mice (FIG. 15a) than in the 5 mice injected with mB7H.P815 (FIG. 15b). These findings indicate that the mB7H-P815 cells were significantly more immunogenic than mock.P815 cells and, therefore, that expression of mB7-H1 expression by P815 cells enhances their ability to elicit protective immunity.

Although the invention has been described with reference to the presently preferred embodiment, it should be understood that various modifications can be made without departing from the spirit of the invention. Accordingly, the invention is limited only by the following claims.

What is claimed is:

1. An isolated DNA comprising:
   (a) a nucleic acid sequence that encodes a polypeptide with the ability to co-stimulate a T cell, wherein the polypeptide is an amino acid sequence consisting of SEQ ID NO:3; or
   (b) the complement of the nucleic acid sequence.

2. The DNA of claim 1, wherein the nucleic acid sequence is a nucleotide sequence consisting of SEQ ID NO:4.

3. A vector comprising the DNA of claim 1.

4. The vector of claim 3, wherein the nucleic acid sequence is operably linked to a regulatory element which allows expression of said nucleic acid sequence in a cell.

5. An isolated cell comprising the vector of claim 3.

6. An isolated cell comprising the vector of claim 4.

7. A method of producing a polypeptide that co-stimulates a T cell, the method comprising culturing the cell of claim 6 and purifying the polypeptide from the culture.

8. An isolated DNA comprising:
   (a) a nucleic acid sequence that encodes a polypeptide consisting of (i) SEQ ID NO: 1 but lacking amino acid residues 1–22 of SEQ ID NO:1 or (ii) SEQ ID NO:3 but lacking amino acid residues 1–22 of SEQ ID NO:3; or
   (b) the complement of the nucleic acid sequence.

9. A vector comprising the DNA of claim 8.

10. The vector of claim 9, wherein the nucleic acid sequence is operably linked to a regulatory element which allows expression of said nucleic acid sequence in a cell.

11. An isolated cell comprising the vector of claim 9.

12. An isolated cell comprising the vector of claim 10.

13. A method of producing a polypeptide that co-stimulates a T cell, the method comprising culturing the cell of claim 12 and purifying the polypeptide from the culture.

* * * * *

UNITED STATES PATENT AND TRADEMARK OFFICE
CERTIFICATE OF CORRECTION

PATENT NO. : 6,803,192 B1
DATED : October 12, 2004
INVENTOR(S) : Lieping Chen, M.D., Ph.D.

It is certified that error appears in the above-identified patent and that said Letters Patent is hereby corrected as shown below:

Column 38,
Lines 46-47, delete:
"(i) SEQ ID NO:1 but lacking amino acid residues 1-22 of SEQ ID NO: 1 or (ii)".

Signed and Sealed this

Twenty-ninth Day of November, 2005

JON W. DUDAS
*Director of the United States Patent and Trademark Office*

SEQUENCE LISTING

<160> NUMBER OF SEQ ID NOS: 12

<210> SEQ ID NO 1
<211> LENGTH: 290
<212> TYPE: PRT
<213> ORGANISM: Homo sapiens

<400> SEQUENCE: 1

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95
```

-continued

```
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
                180                 185                 190
Val Thr Ser Thr Leu Arg Ile Asn Thr Thr Thr Asn Glu Ile Phe Tyr
                195                 200                 205
Cys Thr Phe Arg Arg Leu Asp Pro Glu Glu Asn His Thr Ala Glu Leu
            210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
    290

<210> SEQ ID NO 2
<211> LENGTH: 870
<212> TYPE: DNA
<213> ORGANISM: Homo sapiens

<400> SEQUENCE: 2
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aggactcac     720 ttggtaattc tgggagccat cttattatgc cttggtgtag cactgacatt catcttccgt     780
ttaagaaaag ggagaatgat ggatgtgaaa aaatgtggca tccaagatac aaactcaaag     840
aagcaaagtg atacacattt ggaggagacg                                      870
```

<210> SEQ ID NO 3
<211> LENGTH: 290
<212> TYPE: PRT
<213> ORGANISM: Mus musculus

<400> SEQUENCE: 3

```
Met Arg Ile Phe Ala Gly Ile Ile Phe Thr Ala Cys Cys His Leu Leu
  1               5                  10                  15

Arg Ala Phe Thr Ile Thr Ala Pro Lys Asp Leu Tyr Val Val Glu Tyr
             20                  25                  30

Gly Ser Asn Val Thr Met Glu Cys Arg Phe Pro Val Glu Arg Glu Leu
         35                  40                  45

Asp Leu Leu Ala Leu Val Val Tyr Trp Glu Lys Glu Asp Glu Gln Val
     50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290
```

<210> SEQ ID NO 4
<211> LENGTH: 873
<212> TYPE: DNA
<213> ORGANISM: Mus musculus
<220> FEATURE:
<221> NAME/KEY: CDS
<222> LOCATION: (1)...(870)

<400> SEQUENCE: 4

```
atg agg ata ttt gct ggc att ata ttc aca gcc tgc tgt cac ttg cta      48
Met Arg Ile Phe Ala Gly Ile Ile Phe Thr Ala Cys Cys His Leu Leu
  1               5                  10                  15
```

| | | |
|---|---|---|
| cgg gcg ttt act atc acg gct cca aag gac ttg tac gtg gtg gag tat<br>Arg Ala Phe Thr Ile Thr Ala Pro Lys Asp Leu Tyr Val Val Glu Tyr<br>20                         25                     30 | 96 | |
| ggc agc aac gtc acg atg gag tgc aga ttc cct gta gaa cgg gag ctg<br>Gly Ser Asn Val Thr Met Glu Cys Arg Phe Pro Val Glu Arg Glu Leu<br>       35                    40                 45 | 144 | |
| gac ctg ctt gcg tta gtg gtg tac tgg gaa aag gaa gat gag caa gtg<br>Asp Leu Leu Ala Leu Val Val Tyr Trp Glu Lys Glu Asp Glu Gln Val<br>50                         55                     60 | 192 | |
| att cag ttt gtg gca gga gag gag gac ctt aag cct cag cac agc aac<br>Ile Gln Phe Val Ala Gly Glu Glu Asp Leu Lys Pro Gln His Ser Asn<br>65                         70                     75                     80 | 240 | |
| ttc agg ggg aga gcc tcg ctg cca aag gac cag ctt ttg aag gga aat<br>Phe Arg Gly Arg Ala Ser Leu Pro Lys Asp Gln Leu Leu Lys Gly Asn<br>                    85                     90                     95 | 288 | |
| gct gcc ctt cag atc aca gac gtc aag ctg cag gac gca ggc gtt tac<br>Ala Ala Leu Gln Ile Thr Asp Val Lys Leu Gln Asp Ala Gly Val Tyr<br>                  100                 105               110 | 336 | |
| tgc tgc ata atc agc tac ggt ggt gcg gac tac aag cga atc acg ctg<br>Cys Cys Ile Ile Ser Tyr Gly Gly Ala Asp Tyr Lys Arg Ile Thr Leu<br>       115                    120                 125 | 384 | |
| aaa gtc aat gcc cca tac cgc aaa atc aac cag aga att tcc gtg gat<br>Lys Val Asn Ala Pro Tyr Arg Lys Ile Asn Gln Arg Ile Ser Val Asp<br>130                      135                 140 | 432 | |
| cca gcc act tct gag cat gaa cta ata tgt cag gcc gag ggt tat cca<br>Pro Ala Thr Ser Glu His Glu Leu Ile Cys Gln Ala Glu Gly Tyr Pro<br>145                      150                 155               160 | 480 | |
| gaa gct gag gta atc tgg aca aac agt gac cac caa ccc gtg agt ggg<br>Glu Ala Glu Val Ile Trp Thr Asn Ser Asp His Gln Pro Val Ser Gly<br>                  165                 170               175 | 528 | |
| aag aga agt gtc acc act tcc cgg aca gag ggg atg ctt ctc aat gtg<br>Lys Arg Ser Val Thr Thr Ser Arg Thr Glu Gly Met Leu Leu Asn Val<br>                    180                 185               190 | 576 | |
| acc agc agt ctg agg gtc aac gcc aca gcg aat gat gtt ttc tac tgt<br>Thr Ser Ser Leu Arg Val Asn Ala Thr Ala Asn Asp Val Phe Tyr Cys<br>           195                    200                 205 | 624 | |
| acg ttt tgg aga tca cag cca ggg caa aac cac aca gcg gag ctg atc<br>Thr Phe Trp Arg Ser Gln Pro Gly Gln Asn His Thr Ala Glu Leu Ile<br>       210                    215                 220 | 672 | |
| atc cca gaa ctg cct gca aca cat cct cca cag aac agg act cac tgg<br>Ile Pro Glu Leu Pro Ala Thr His Pro Pro Gln Asn Arg Thr His Trp<br>225                      230                 235               240 | 720 | |
| gtg ctt ctg gga tcc atc ctg ttg ttc ctc att gta gtg tcc acg gtc<br>Val Leu Leu Gly Ser Ile Leu Leu Phe Leu Ile Val Val Ser Thr Val<br>                    245                 250               255 | 768 | |
| ctc ctc ttc ttg aga aaa caa gtg aga atg cta gat gtg gag aaa tgt<br>Leu Leu Phe Leu Arg Lys Gln Val Arg Met Leu Asp Val Glu Lys Cys<br>           260                    265                 270 | 816 | |
| ggc gtt gaa gat aca agc tca aaa aac cga aat gat aca caa ttc gag<br>Gly Val Glu Asp Thr Ser Ser Lys Asn Arg Asn Asp Thr Gln Phe Glu<br>       275                    280                 285 | 864 | |
| gag acg taa<br>Glu Thr<br>      290 | 873 | |

<210> SEQ ID NO 5
<211> LENGTH: 3616
<212> TYPE: DNA
<213> ORGANISM: Homo sapiens
<220> FEATURE:
<221> NAME/KEY: CDS -continued

```
<222> LOCATION: (73)...(942)

<400> SEQUENCE: 5
cccacgcgtc cgcagcttcc cgaggctccg caccagccgc gcttctgtcc gcctgcaggg        60
cattccagaa ag atg agg ata ttt gct gtc ttt ata ttc atg acc tac tgg      111
          Met Arg Ile Phe Ala Val Phe Ile Phe Met Thr Tyr Trp
            1               5                  10 cat ttg ctg aac gca ttt act gtc acg gtt ccc aag gac cta tat gtg       159
His Leu Leu Asn Ala Phe Thr Val Thr Val Pro Lys Asp Leu Tyr Val
 15                  20                  25 gta gag tat ggt agc aat atg aca att gaa tgc aaa ttc cca gta gaa       207
Val Glu Tyr Gly Ser Asn Met Thr Ile Glu Cys Lys Phe Pro Val Glu
 30                  35                  40                  45 aaa caa tta gac ctg gct gca cta att gtc tat tgg gaa atg gag gat       255
Lys Gln Leu Asp Leu Ala Ala Leu Ile Val Tyr Trp Glu Met Glu Asp
                 50                  55                  60 aag aac att att caa ttt gtg cat gga gag gaa gac ctg aag gtt cag       303
Lys Asn Ile Ile Gln Phe Val His Gly Glu Glu Asp Leu Lys Val Gln
             65                  70                  75 cat agt agc tac aga cag agg gcc cgg ctg ttg aag gac cag ctc tcc       351
His Ser Ser Tyr Arg Gln Arg Ala Arg Leu Leu Lys Asp Gln Leu Ser
         80                  85                  90 ctg gga aat gct gca ctt cag atc aca gat gtg aaa ttg cag gat gca       399
Leu Gly Asn Ala Ala Leu Gln Ile Thr Asp Val Lys Leu Gln Asp Ala
     95                 100                 105 ggg gtg tac cgc tgc atg atc agc tat ggt ggt gcc gac tac aag cga       447
Gly Val Tyr Arg Cys Met Ile Ser Tyr Gly Gly Ala Asp Tyr Lys Arg
110                 115                 120                 125 att act gtg aaa gtc aat gcc cca tac aac aaa atc aac caa aga att       495
Ile Thr Val Lys Val Asn Ala Pro Tyr Asn Lys Ile Asn Gln Arg Ile
                130                 135                 140 ttg gtt gtg gat cca gtc acc tct gaa cat gaa ctg aca tgt cag gct       543
Leu Val Val Asp Pro Val Thr Ser Glu His Glu Leu Thr Cys Gln Ala
            145                 150                 155 gag ggc tac ccc aag gcc gaa gtc atc tgg aca agc agt gac cat caa       591
Glu Gly Tyr Pro Lys Ala Glu Val Ile Trp Thr Ser Ser Asp His Gln
        160                 165                 170 gtc ctg agt ggt aag acc acc acc acc aat tcc aag aga gag gag aag       639
Val Leu Ser Gly Lys Thr Thr Thr Thr Asn Ser Lys Arg Glu Glu Lys
    175                 180                 185 ctt ttc aat gtg acc agc aca ctg aga atc aac aca aca act aat gag       687
Leu Phe Asn Val Thr Ser Thr Leu Arg Ile Asn Thr Thr Thr Asn Glu
190                 195                 200                 205 att ttc tac tgc act ttt agg aga tta gat cct gag gaa aac cat aca       735
Ile Phe Tyr Cys Thr Phe Arg Arg Leu Asp Pro Glu Glu Asn His Thr
                210                 215                 220 gct gaa ttg gtc atc cca gaa cta cct ctg gca cat cct cca aat gaa       783
Ala Glu Leu Val Ile Pro Glu Leu Pro Leu Ala His Pro Pro Asn Glu
            225                 230                 235 agg act cac ttg gta att ctg gga gcc atc tta tta tgc ctt ggt gta       831
Arg Thr His Leu Val Ile Leu Gly Ala Ile Leu Leu Cys Leu Gly Val
        240                 245                 250 gca ctg aca ttc atc ttc cgt tta aga aaa ggg aga atg atg gat gtg       879
Ala Leu Thr Phe Ile Phe Arg Leu Arg Lys Gly Arg Met Met Asp Val
    255                 260                 265 aaa aaa tgt ggc atc caa gat aca aac tca aag aag caa agt gat aca       927
Lys Lys Cys Gly Ile Gln Asp Thr Asn Ser Lys Lys Gln Ser Asp Thr
270                 275                 280                 285 cat ttg gag gag acg taatccagca ttggaacttc tgatcttcaa gcagggattc        982
His Leu Glu Glu Thr
```

```
His Leu Glu Glu Thr
            290 tcaacctgtg gtttaggggt tcatcggggc tgagcgtgac aagaggaagg aatggacccg   1042 tgggatgcag gcaatgtggg acttaaaagg cccaagcact gaaaatggaa cctggcgaaa   1102 gcagaggagg agaatgaaga aagatggagt caaacaggga gcctggaggg agaccttgat   1162 actttcaaat gcctgagggg ctcatcgacg cctgtgacag ggagaaagga tacttctgaa   1222 caaggagcct ccaagcaaat catccattgc tcatcctagg aagacgggtt gagaatccct   1282 aatttgaggg tcagttcctg cagaagtgcc ctttgcctcc actcaatgcc tcaatttctt   1342 ttctgcatga ctgagagtct cagtgttgga acgggacagt atttatgtat gagttttttcc  1402 tatttatttt gagtctgtga ggtcttcttg tcatgtgagt gtggttgtga atgatttctt   1462 ttgaagatat attgtagtag atgttacaat tttgtcgcca aactaaactt gctgcttaat   1522 gatttgctca catctagtaa acatggagt atttgtaagg tgcttggtct cctctataac    1582 tacaagtata cattggaagc ataaagatca aaccgttggt tgcataggat gtcacccttta  1642 tttaacccat taatactctg gttgacctaa tcttattctc agacctcaag tgtctgtgca   1702 gtatctgttc catttaaata tcagctttac aattatgtgg tagcctacac acataatctc   1762 atttcatcgc tgtaaccacc ctgttgtgat aaccactatt attttaccca tcgtacagct   1822 gaggaagcaa acagattaag taacttgccc aaaccagtaa atagcagacc tcagactgcc   1882 acccactgtc cttttataat acaatttaca gctatatttt actttaagca attcttttat   1942 tcaaaaacca tttattaagt gcccttgcaa tatcaatcgc tgtgccaggc attgaatcta   2002 cagatgtgag caagacaaag tacctgtcct caaggagctc atagtataat gaggagatta   2062 acaagaaaat gtattattac aatttagtcc agtgtcatag cataaggatg atgcgagggg   2122 aaaacccgag cagtgttgcc aagaggagga ataggccaa tgtggtctgg gacggttgga    2182 tatacttaaa catcttaata atcagagtaa ttttcattta caaagagagg tcggtactta   2242 aaataacccct gaaaaataac actggaattc cttttctagc attatattta ttcctgattt   2302 gcctttgcca tataatctaa tgcttgttta tatagtgtct ggtattgttt aacagttctg   2362 tcttttctat ttaaatgcca ctaaatttta aattcatacc tttccatgat tcaaaattca   2422 aaagatccca tgggagatgg ttggaaaatc tccacttcat cctccaagcc attcaagttt   2482 cctttccaga agcaactgct actgcctttc attcatatgt tcttctaaag atagtctaca   2542 tttgaaatg tatgttaaaa gcacgtattt ttaaaatttt tttcctaaat agtaacacat     2602 tgtatgtctg ctgtgtactt tgctatttt atttatttta gtgtttctta tatagcagat    2662 ggaatgaatt tgaagttccc agggctgagg atccatgcct tctttgtttc taagttatct   2722 ttcccatagc ttttcattat ctttcatatg atccagtata tgttaaatat gtcctacata   2782 tacatttaga caaccaccat tgttaagta tttgctctag gacagagttt ggatttgttt    2842 atgtttgctc aaaaggagac ccatgggctc tccagggtgc actgagtcaa tctagtccta   2902 aaaagcaatc ttattattaa ctctgtatga cagaatcatg tctggaactt ttgtttttctg  2962 cttttctgtca agtataaact tcactttgat gctgtacttg caaaatcaca ttttcttttct  3022 ggaaattccg gcagtgtacc ttgactgcta gctaccctgt gccagaaaag cctcattcgt   3082 tgtgcttgaa cccttgaatg ccaccagctg tcatcactac acagccctcc taagaggctt   3142 cctggaggtt tcgagattca gatgccctgg gagatcccag agtttccttt ccctcttggc   3202 catattctgg tgtcaatgac aaggagtacc ttggctttgc cacatgtcaa ggctgaagaa   3262
```

```
acagtgtctc caacagagct ccttgtgtta tctgtttgta catgtgcatt tgtacagtaa    3322
ttggtgtgac agtgttcttt gtgtgaatta caggcaagaa ttgtggctga gcaaggcaca    3382
tagtctactc agtctattcc taagtcctaa ctcctccttg tggtgttgga tttgtaaggc    3442
actttatccc ttttgtctca tgtttcatcg taaatggcat aggcagagat gatacctaat    3502
tctgcatttg attgtcactt tttgtacctg cattaattta ataaaatatt cttatttatt    3562
ttgttacttg gtaaaaaaaa aaaaaaaaaa aaaaaaaaaa aaaaaaaaaa aaaa          3616
```

<210> SEQ ID NO 6
<211> LENGTH: 25
<212> TYPE: PRT
<213> ORGANISM: Homo sapiens

<400> SEQUENCE: 6

Met Ala Ile Ser Gly Val Pro Val Leu Gly Phe Phe Ile Ile Ala Val
 1               5                  10                  15

Leu Met Ser Ala Gln Glu Ser Trp Ala
            20                  25

<210> SEQ ID NO 7
<211> LENGTH: 5
<212> TYPE: PRT
<213> ORGANISM: Bovidae

<400> SEQUENCE: 7

Lys Phe Glu Arg Gln
 1               5

<210> SEQ ID NO 8
<211> LENGTH: 15
<212> TYPE: PRT
<213> ORGANISM: Homo sapiens

<400> SEQUENCE: 8

Met Asp Asp Gln Arg Asp Leu Ile Ser Asn Asn Glu Gln Leu Pro
 1               5                  10                  15

<210> SEQ ID NO 9
<211> LENGTH: 4
<212> TYPE: PRT
<213> ORGANISM: Rattus rattus

<400> SEQUENCE: 9

Lys Asp Glu Leu
 1

<210> SEQ ID NO 10
<211> LENGTH: 210
<212> TYPE: PRT
<213> ORGANISM: Homo sapiens

<400> SEQUENCE: 10

Val Glu Tyr Gly Ser Asn Met Thr Ile Glu Cys Lys Phe Pro Val Glu
 1               5                  10                  15

Lys Gln Leu Asp Leu Ala Ala Leu Ile Val Tyr Trp Glu Met Glu Asp
            20                  25                  30

Lys Asn Ile Ile Gln Phe Val His Gly Glu Glu Asp Leu Lys Val Gln
        35                  40                  45

His Ser Ser Tyr Arg Gln Arg Ala Arg Leu Leu Lys Asp Gln Leu Ser
    50                  55                  60

-continued

Leu Gly Asn Ala Ala Leu Gln Ile Thr Asp Val Lys Leu Gln Asp Ala
 65                  70                  75                  80

Gly Val Tyr Arg Cys Met Ile Ser Tyr Gly Ala Asp Tyr Lys Arg
                 85                  90                  95

Ile Thr Val Lys Val Asn Ala Pro Tyr Asn Lys Ile Asn Gln Arg Ile
                100                 105                 110

Leu Val Val Asp Pro Val Thr Ser Glu His Glu Leu Thr Cys Gln Ala
                115                 120                 125

Glu Gly Tyr Pro Lys Ala Glu Val Ile Trp Thr Ser Ser Asp His Gln
            130                 135                 140

Val Leu Ser Gly Lys Thr Thr Thr Asn Ser Lys Arg Glu Glu Lys
145                 150                 155                 160

Leu Phe Asn Val Thr Ser Thr Leu Arg Ile Asn Thr Thr Thr Asn Glu
                165                 170                 175

Ile Phe Tyr Cys Thr Phe Arg Arg Leu Asp Pro Glu Glu Asn His Thr
                180                 185                 190

Ala Glu Leu Val Ile Pro Glu Leu Pro Leu Ala His Pro Pro Asn Glu
            195                 200                 205

Arg Thr
    210

<210> SEQ ID NO 11
<211> LENGTH: 205
<212> TYPE: PRT
<213> ORGANISM: Homo sapiens

<400> SEQUENCE: 11

Lys Glu Val Lys Glu Val Ala Thr Leu Ser Cys Gly His Asn Val Ser
  1               5                  10                  15

Val Glu Glu Leu Ala Gln Thr Arg Ile Tyr Trp Gln Lys Glu Lys Lys
                 20                  25                  30

Met Val Leu Thr Met Met Ser Gly Asp Met Asn Ile Trp Pro Glu Tyr
                 35                  40                  45

Lys Asn Arg Thr Ile Phe Asp Ile Thr Asn Asn Leu Ser Ile Val Ile
             50                  55                  60

Leu Ala Leu Arg Pro Ser Asp Glu Gly Thr Tyr Glu Cys Val Val Leu
 65                  70                  75                  80

Lys Tyr Glu Lys Asp Ala Phe Lys Arg Glu His Leu Ala Glu Val Thr
                 85                  90                  95

Leu Ser Val Lys Ala Asp Phe Pro Thr Pro Ser Ile Ser Asp Phe Glu
                100                 105                 110

Ile Pro Thr Ser Asn Ile Arg Arg Ile Ile Cys Ser Thr Ser Gly Gly
            115                 120                 125

Phe Pro Glu Pro His Leu Ser Trp Leu Glu Asn Gly Glu Glu Leu Asn
130                 135                 140

Ala Ile Asn Thr Thr Val Ser Gln Asp Pro Glu Thr Glu Leu Tyr Ala
145                 150                 155                 160

Val Ser Ser Lys Leu Asp Phe Asn Met Thr Thr Asn His Ser Phe Met
                165                 170                 175

Cys Leu Ile Lys Tyr Gly His Leu Arg Val Asn Gln Thr Phe Asn Trp
                180                 185                 190

Asn Thr Thr Lys Gln Glu His Phe Pro Asp Asn Leu Leu
            195                 200                 205

<210> SEQ ID NO 12

```
-continued

<211> LENGTH: 218
<212> TYPE: PRT
<213> ORGANISM: Homo sapiens

<400> SEQUENCE: 12

Ala Tyr Phe Asn Glu Thr Ala Asp Leu Pro Cys Gln Phe Ala Asn Ser
 1               5                  10                  15

Gln Asn Gln Ser Leu Ser Glu Leu Val Val Phe Trp Gln Asp Gln Glu
            20                  25                  30

Asn Leu Val Leu Asn Glu Val Tyr Leu Gly Lys Glu Lys Phe Asp Ser
        35                  40                  45

Val His Ser Lys Tyr Met Gly Arg Thr Ser Phe Asp Ser Asp Ser Trp
 50                  55                  60

Thr Leu Arg Leu His Asn Leu Gln Ile Lys Asp Lys Gly Leu Tyr Gln
 65                  70                  75                  80

Cys Ile Ile His His Lys Lys Pro Thr Gly Met Ile Arg Ile His Gln
                85                  90                  95

Met Asn Ser Glu Leu Ser Val Leu Ala Asn Phe Ser Gln Pro Glu Ile
            100                 105                 110

Val Pro Ile Ser Asn Ile Thr Glu Asn Val Tyr Ile Asn Leu Thr Cys
        115                 120                 125

Ser Ser Ile His Gly Tyr Pro Glu Pro Lys Lys Met Ser Val Leu Leu
130                 135                 140

Arg Thr Lys Asn Ser Thr Ile Glu Tyr Asp Gly Ile Met Gln Lys Ser
145                 150                 155                 160

Gln Asp Asn Val Thr Glu Leu Tyr Asp Val Ser Ile Ser Leu Ser Val
                165                 170                 175

Ser Phe Pro Asp Val Thr Ser Asn Met Thr Ile Phe Cys Ile Leu Glu
            180                 185                 190

Thr Asp Lys Thr Arg Leu Leu Ser Ser Pro Phe Ser Ile Glu Leu Glu
        195                 200                 205

Asp Pro Gln Pro Pro Asp His Ile Pro
210                 215
```